US010806942B2

(12) United States Patent
Hochstenbach

(10) Patent No.: US 10,806,942 B2
(45) Date of Patent: Oct. 20, 2020

(54) SYSTEM AND METHOD FOR APPLYING A LOW FREQUENCY MAGNETIC FIELD TO BIOLOGICAL TISSUES

(71) Applicant: Qoravita LLC, Milpitas, CA (US)

(72) Inventor: Francis Hochstenbach, Milpitas, CA (US)

(*) Notice: Subject to any disclaimer, the term of this patent is extended or adjusted under 35 U.S.C. 154(b) by 276 days.

(21) Appl. No.: 15/809,689

(22) Filed: Nov. 10, 2017

(65) Prior Publication Data

US 2018/0126185 A1 May 10, 2018

Related U.S. Application Data

(60) Provisional application No. 62/420,337, filed on Nov. 10, 2016.

(51) Int. Cl.
*A61N 2/02* (2006.01)

(52) U.S. Cl.
CPC ..................... *A61N 2/02* (2013.01)

(58) Field of Classification Search
CPC ........................................................ A61N 2/02
See application file for complete search history.

(56) References Cited

U.S. PATENT DOCUMENTS

| 2,648,727 | A | 8/1953 | Rockwell et al. |
|---|---|---|---|
| 3,043,310 | A | 7/1962 | Milinowski et al. |
| 3,181,535 | A | 5/1965 | Milinowski et al. |
| 3,270,746 | A | 9/1966 | Denis et al. |
| 3,329,148 | A | 7/1967 | Denis et al. |
| 3,329,149 | A | 7/1967 | Denis et al. |
| 3,658,051 | A | 4/1972 | Maclean et al. |
| 3,797,500 | A | 3/1974 | Porter |
| 3,800,802 | A | 4/1974 | Berry et al. |

(Continued)

FOREIGN PATENT DOCUMENTS

| EP | 1216076 | 6/2002 |
|---|---|---|
| KR | 101219990 | 1/2013 |

(Continued)

OTHER PUBLICATIONS

PCT Written Opinion/ISR PCT/US2017/061106 (dated Feb. 28, 2018).

*Primary Examiner* — Christine H Matthews
*Assistant Examiner* — Joshua Daryl D Lannu
(74) *Attorney, Agent, or Firm* — Hoffberg & Associates; Steven M. Hoffberg

(57) ABSTRACT

A system and method for applying a low strength, low frequency magnetic field therapy to biological tissues. A coil is excited with a low frequency oscillating current, e.g., 10-1000 Hz. The coil is, e.g., 5-200 turns, having a diameter of 2-20 mm, and produces a magnetic field strength of about 0.01-5 mTelsa at a distance of 1 cm from the coil, or a cover over the coil, into the tissue. The current is preferably controlled by a smartphone or other programmable device controlled by a downloadable app in accordance with a PEMF program which may be separately downloaded or updated, and may be provided through an audio jack. Alternately, a digital interface and/or wireless interface may control the current. An app on the smartphone may be used to control the frequency, amplitude/envelope modulation, waveform, duration, etc. of the oscillation. The coil may be in mineral housing with a simple filter, and TRRS-type audio jack.

20 Claims, 1 Drawing Sheet

(56) References Cited

U.S. PATENT DOCUMENTS

| | | |
|---|---|---|
| 3,820,888 A | 6/1974 | Jordon et al. |
| 3,890,953 A | 6/1975 | Kraus et al. |
| 3,893,462 A | 7/1975 | Manning |
| 3,902,502 A | 9/1975 | Liss et al. |
| 3,915,151 A | 10/1975 | Kraus |
| 3,952,751 A | 4/1976 | Yarger |
| 3,978,864 A | 9/1976 | Smith |
| 4,028,518 A | 6/1977 | Boudouris et al. |
| 4,095,588 A | 6/1978 | Goldman et al. |
| 4,105,017 A | 8/1978 | Ryaby et al. |
| 4,128,824 A | 12/1978 | Mirsch |
| 4,177,796 A | 12/1979 | Franco-Vila |
| 4,197,851 A | 4/1980 | Fellus |
| 4,233,965 A | 11/1980 | Fairbanks |
| 4,266,532 A | 5/1981 | Ryaby et al. |
| 4,305,115 A | 12/1981 | Armitage |
| 4,315,503 A | 2/1982 | Ryaby et al. |
| 4,338,945 A | 7/1982 | Kosugi et al. |
| 4,340,063 A | 7/1982 | Maurer |
| 4,374,482 A | 2/1983 | Moore et al. |
| 4,428,366 A | 1/1984 | Findl et al. |
| 4,454,882 A | 6/1984 | Takano |
| 4,461,300 A | 7/1984 | Christensen |
| 4,479,388 A | 10/1984 | Matzuk |
| 4,548,208 A | 10/1985 | Niemi |
| 4,550,714 A | 11/1985 | Talish et al. |
| 4,556,051 A | 12/1985 | Maurer |
| 4,586,509 A | 5/1986 | Liss et al. |
| 4,616,629 A | 10/1986 | Moore |
| 4,627,438 A | 12/1986 | Liss et al. |
| 4,641,633 A | 2/1987 | Delgado |
| 4,654,574 A | 3/1987 | Thaler |
| 4,672,951 A | 6/1987 | Welch |
| 4,674,482 A | 6/1987 | Waltonen et al. |
| 4,765,310 A | 8/1988 | Deagle et al. |
| 4,793,325 A | 12/1988 | Cadossi et al. |
| 4,829,984 A | 5/1989 | Gordon |
| 4,850,372 A | 7/1989 | Ko et al. |
| 4,889,526 A | 12/1989 | Rauscher et al. |
| 4,911,686 A | 3/1990 | Thaler |
| 4,926,881 A | 5/1990 | Ichinomiya et al. |
| 4,937,323 A | 6/1990 | Silver et al. |
| 4,940,453 A | 7/1990 | Cadwell |
| 4,942,880 A | 7/1990 | Slovak |
| 4,993,413 A | 2/1991 | McLeod et al. |
| 4,998,532 A | 3/1991 | Griffith |
| 5,000,000 A | 3/1991 | Ingram et al. |
| 5,000,178 A | 3/1991 | Griffith |
| 5,001,000 A | 3/1991 | Rohrbacher et al. |
| 5,008,561 A | 4/1991 | Madeley et al. |
| 5,014,699 A | 5/1991 | Pollack et al. |
| 5,058,582 A | 10/1991 | Thaler |
| 5,116,304 A | 5/1992 | Cadwell |
| 5,123,898 A | 6/1992 | Liboff et al. |
| 5,147,284 A | 9/1992 | Fedorov et al. |
| 5,181,902 A | 1/1993 | Erickson et al. |
| 5,195,941 A | 3/1993 | Erickson et al. |
| 5,224,922 A | 7/1993 | Kurtz |
| 5,269,747 A | 12/1993 | Erickson et al. |
| 5,273,033 A | 12/1993 | Hoffman |
| 5,314,401 A | 5/1994 | Tepper |
| 5,338,286 A | 8/1994 | Abbott et al. |
| 5,351,389 A | 10/1994 | Erickson et al. |
| 5,370,680 A | 12/1994 | Proctor |
| 5,386,837 A | 2/1995 | Sterzer |
| 5,401,233 A | 3/1995 | Erickson et al. |
| 5,407,421 A | 4/1995 | Goldsmith |
| 5,441,495 A | 8/1995 | Liboff et al. |
| 5,441,527 A | 8/1995 | Erickson et al. |
| 5,478,303 A | 12/1995 | Foley-Nolan et al. |
| 5,480,373 A | 1/1996 | Fischer et al. |
| 5,514,175 A | 5/1996 | Kim et al. |
| 5,518,496 A | 5/1996 | McLeod et al. |
| 5,529,569 A | 6/1996 | Woo |
| 5,544,665 A * | 8/1996 | Litovitz ............. A61N 1/16 128/897 |
| 5,565,005 A | 10/1996 | Erickson et al. |
| 5,584,863 A | 12/1996 | Rauch et al. |
| 5,595,564 A | 1/1997 | Pinna |
| 5,703,735 A | 12/1997 | Bleeke |
| 5,707,334 A | 1/1998 | Young |
| 5,718,246 A | 2/1998 | Vona |
| 5,718,721 A | 2/1998 | Ross |
| 5,723,001 A | 3/1998 | Pilla et al. |
| 5,743,844 A | 4/1998 | Tepper et al. |
| 5,766,231 A | 6/1998 | Erickson et al. |
| 5,778,894 A | 7/1998 | Dorogi et al. |
| 5,792,209 A | 8/1998 | Varner |
| 5,814,078 A | 9/1998 | Zhou et al. |
| 5,877,627 A | 3/1999 | Fischer et al. |
| 5,908,444 A | 6/1999 | Azure |
| 5,951,459 A | 9/1999 | Blackwell |
| 5,960,500 A | 10/1999 | Bolton |
| 5,960,513 A | 10/1999 | Beshah |
| 5,968,527 A | 10/1999 | Litovitz |
| 5,983,134 A | 11/1999 | Ostrow |
| 5,990,177 A | 11/1999 | Brown |
| 5,997,464 A | 12/1999 | Blackwell |
| 6,004,257 A | 12/1999 | Jacobson |
| 6,011,994 A | 1/2000 | Kronberg |
| 6,024,691 A | 2/2000 | Tepper et al. |
| 6,029,084 A | 2/2000 | Long et al. |
| 6,048,302 A | 4/2000 | Markoll |
| 6,075,603 A | 6/2000 | O'Meara et al. |
| 6,083,149 A | 7/2000 | Wascher et al. |
| 6,086,525 A | 7/2000 | Davey et al. |
| 6,087,652 A | 7/2000 | O'Meara et al. |
| 6,099,459 A | 8/2000 | Jacobson |
| 6,132,361 A | 10/2000 | Epstein et al. |
| 6,132,362 A | 10/2000 | Tepper et al. |
| 6,149,577 A | 11/2000 | Bouldin et al. |
| 6,155,966 A | 12/2000 | Parker |
| 6,169,963 B1 | 1/2001 | Markov |
| 6,174,276 B1 | 1/2001 | Blackwell |
| 6,179,772 B1 | 1/2001 | Blackwell |
| 6,186,941 B1 | 2/2001 | Blackwell |
| 6,190,893 B1 | 2/2001 | Shastri et al. |
| 6,200,259 B1 | 3/2001 | March |
| 6,213,934 B1 | 4/2001 | Bianco et al. |
| 6,217,604 B1 | 4/2001 | Azure et al. |
| 6,231,187 B1 | 5/2001 | Munoz et al. |
| 6,231,528 B1 | 5/2001 | Kaufman et al. |
| 6,234,953 B1 | 5/2001 | Thomas et al. |
| 6,246,912 B1 | 6/2001 | Sluijter et al. |
| 6,261,221 B1 | 7/2001 | Tepper et al. |
| 6,261,831 B1 | 7/2001 | Agee |
| 6,285,514 B1 | 9/2001 | O'Meara et al. |
| 6,301,506 B1 | 10/2001 | den Boer et al. |
| 6,321,119 B1 | 11/2001 | Kronberg |
| 6,321,120 B1 | 11/2001 | Surbeck et al. |
| 6,334,069 B1 | 12/2001 | George et al. |
| 6,348,070 B1 | 2/2002 | Teissl et al. |
| 6,371,905 B1 | 4/2002 | March |
| 6,418,345 B1 | 7/2002 | Tepper et al. |
| 6,421,562 B1 | 7/2002 | Ross |
| 6,424,863 B1 | 7/2002 | Flock et al. |
| 6,425,852 B1 | 7/2002 | Epstein et al. |
| 6,434,426 B1 | 8/2002 | Munneke et al. |
| 6,443,883 B1 | 9/2002 | Ostrow et al. |
| 6,450,941 B1 | 9/2002 | Larsen |
| 6,458,151 B1 | 10/2002 | Saltiel |
| 6,458,157 B1 | 10/2002 | Suaning |
| 6,463,336 B1 | 10/2002 | Mawhinney |
| 6,535,767 B1 | 3/2003 | Kronberg |
| 6,556,872 B2 | 4/2003 | Hauck |
| 6,560,489 B2 | 5/2003 | Hauck |
| 6,561,968 B1 | 5/2003 | Dissing et al. |
| 6,564,093 B1 | 5/2003 | Ostrow et al. |
| 6,569,654 B2 | 5/2003 | Shastri et al. |
| 6,589,159 B2 | 7/2003 | Paturu |
| 6,629,971 B2 | 10/2003 | McDaniel |
| 6,647,301 B1 | 11/2003 | Sederlund et al. |
| 6,648,812 B2 | 11/2003 | Ardizzone |

(56) References Cited

U.S. PATENT DOCUMENTS

| | | |
|---|---|---|
| 6,652,473 B2 | 11/2003 | Kaufman et al. |
| 6,675,047 B1 | 1/2004 | Konoplev et al. |
| 6,678,562 B1 | 1/2004 | Tepper et al. |
| 6,684,108 B2 | 1/2004 | Surbeck et al. |
| 6,701,185 B2 | 3/2004 | Burnett et al. |
| 6,819,210 B2 | 11/2004 | Boynton et al. |
| 6,839,589 B2 | 1/2005 | Petlan |
| 6,839,595 B2 | 1/2005 | Tepper et al. |
| 6,844,378 B1 | 1/2005 | Martin et al. |
| 6,853,864 B2 | 2/2005 | Litovitz |
| 6,856,839 B2 | 2/2005 | Litovitz |
| 6,895,282 B2 | 5/2005 | Gellman et al. |
| 6,919,205 B2 | 7/2005 | Brighton |
| 6,934,580 B1 | 8/2005 | Osorio et al. |
| 6,955,642 B1 | 10/2005 | Simon |
| 6,995,013 B2 | 2/2006 | Connelly et al. |
| 7,010,353 B2 | 3/2006 | Gan et al. |
| 7,022,506 B2 | 4/2006 | Brighton et al. |
| 7,039,467 B2 | 5/2006 | Hauck |
| 7,089,060 B1 | 8/2006 | Fitzsimmons |
| 7,113,830 B2 | 9/2006 | Hauck |
| 7,117,034 B2 | 10/2006 | Kronberg |
| 7,130,692 B2 | 10/2006 | Brighton et al. |
| 7,158,835 B2 | 1/2007 | Brighton et al. |
| 7,160,241 B1 | 1/2007 | Herbst |
| 7,162,303 B2 | 1/2007 | Levin et al. |
| 7,167,753 B2 | 1/2007 | Brighton et al. |
| 7,175,587 B2 | 2/2007 | Gordon et al. |
| 7,177,695 B2 | 2/2007 | Moran |
| 7,177,696 B1 | 2/2007 | Pandelisev |
| 7,215,995 B2 | 5/2007 | Brighton et al. |
| 7,228,178 B2 | 6/2007 | Carroll et al. |
| 7,280,861 B2 | 10/2007 | Thomas et al. |
| 7,288,062 B2 | 10/2007 | Spiegel |
| 7,333,858 B2 | 2/2008 | Killian et al. |
| 7,354,393 B2 | 4/2008 | Ardizzone et al. |
| 7,354,748 B2 | 4/2008 | Brighton |
| 7,361,136 B2 | 4/2008 | Parker |
| 7,367,988 B1 | 5/2008 | Litovitz |
| 7,374,916 B2 | 5/2008 | Brighton |
| 7,419,474 B2 | 9/2008 | Lee |
| 7,429,471 B2 | 9/2008 | Brighton |
| 7,456,189 B2 | 11/2008 | Himmelsbach et al. |
| 7,465,546 B2 | 12/2008 | Brighton |
| 7,465,566 B2 | 12/2008 | Brighton et al. |
| 7,468,264 B2 | 12/2008 | Brighton et al. |
| 7,507,198 B2 | 3/2009 | Ardizzone et al. |
| 7,513,906 B2 | 4/2009 | Passy et al. |
| 7,517,311 B1 | 4/2009 | Herbst |
| 7,520,849 B1 | 4/2009 | Simon |
| 7,551,957 B2 | 6/2009 | Whelan et al. |
| 7,563,224 B2 | 7/2009 | Puchek |
| 7,564,267 B1 | 7/2009 | Patterson |
| 7,566,295 B2 | 7/2009 | Giardino et al. |
| 7,587,230 B2 | 9/2009 | Litovitz |
| 7,602,218 B2 | 10/2009 | Patterson |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,659,750 B2 | 2/2010 | Patterson |
| 7,662,615 B2 | 2/2010 | Chang et al. |
| 7,696,860 B2 | 4/2010 | Gilson et al. |
| 7,717,948 B2 | 5/2010 | Demarais et al. |
| RE41,391 E | 6/2010 | Brighton |
| 7,740,574 B2 | 6/2010 | Pilla et al. |
| 7,744,524 B2 | 6/2010 | Pilla |
| 7,744,869 B2 | 6/2010 | Simon |
| 7,758,490 B2 | 7/2010 | Pilla et al. |
| 7,768,338 B2 | 8/2010 | Patterson |
| 7,783,348 B2 | 8/2010 | Gill et al. |
| 7,797,552 B2 | 9/2010 | Kahn et al. |
| 7,819,794 B2 | 10/2010 | Becker |
| 7,829,535 B2 | 11/2010 | O'Connor |
| 7,840,272 B2 | 11/2010 | Kronberg et al. |
| 7,842,432 B2 | 11/2010 | Niu et al. |
| 7,867,235 B2 | 1/2011 | Fell et al. |
| 7,896,797 B2 | 3/2011 | Pilla et al. |
| 7,937,143 B2 | 5/2011 | Demarais et al. |
| 7,939,218 B2 | 5/2011 | Niu |
| 7,981,611 B2 | 7/2011 | Brighton |
| 7,988,613 B2 | 8/2011 | Becker |
| 8,014,846 B2 | 9/2011 | Litovitz |
| 8,017,369 B2 | 9/2011 | Brighton |
| 8,029,432 B2 | 10/2011 | Dennis et al. |
| 8,039,031 B2 | 10/2011 | Baianu et al. |
| 8,060,210 B1 | 11/2011 | Carroll |
| 8,065,015 B2 | 11/2011 | Brighton et al. |
| 8,070,703 B2 | 12/2011 | Skahan et al. |
| 8,079,966 B2 | 12/2011 | El-Bialy et al. |
| 8,131,371 B2 | 3/2012 | Demarals et al. |
| 8,131,372 B2 | 3/2012 | Levin et al. |
| 8,142,774 B2 | 3/2012 | Simon |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,167,784 B1 | 5/2012 | Honeycutt et al. |
| 8,175,711 B2 | 5/2012 | Demarais et al. |
| 8,292,834 B2 | 10/2012 | El-Bialy et al. |
| 8,313,908 B2 | 11/2012 | Brighton |
| 8,343,027 B1 | 1/2013 | DiMino et al. |
| 8,346,367 B2 | 1/2013 | Carroll |
| 8,347,891 B2 | 1/2013 | Demarais et al. |
| 8,376,925 B1 | 2/2013 | Dennis et al. |
| 8,412,328 B2 | 4/2013 | Whelan et al. |
| 8,412,346 B2 | 4/2013 | Gellman et al. |
| 8,415,123 B2 | 4/2013 | Pilla et al. |
| 8,430,805 B2 | 4/2013 | Burnett et al. |
| 8,433,423 B2 | 4/2013 | Demarais |
| 8,435,166 B2 | 5/2013 | Burnett et al. |
| 8,444,640 B2 | 5/2013 | Demarais et al. |
| 8,454,543 B2 | 6/2013 | Skahan et al. |
| 8,454,594 B2 | 6/2013 | Demarais et al. |
| 8,460,167 B2 | 6/2013 | Chornenky et al. |
| 8,477,003 B2 | 7/2013 | Wilson et al. |
| 8,478,422 B2 | 7/2013 | Epstein et al. |
| 8,548,600 B2 | 10/2013 | Deem et al. |
| 8,551,069 B2 | 10/2013 | Demarais et al. |
| 8,560,077 B2 | 10/2013 | Feinstein |
| 8,569,050 B1 | 10/2013 | Ericsson |
| 8,571,642 B2 | 10/2013 | Gill et al. |
| 8,600,514 B1 | 12/2013 | Carroll |
| 8,620,423 B2 | 12/2013 | Demarais et al. |
| 8,626,300 B2 | 1/2014 | Demarais et al. |
| 8,657,732 B2 | 2/2014 | Vasishta |
| 8,682,448 B2 | 3/2014 | Weinstock |
| 8,684,998 B2 | 4/2014 | Demarais et al. |
| 8,721,637 B2 | 5/2014 | Zarins et al. |
| 8,728,137 B2 | 5/2014 | Zarins et al. |
| 8,728,138 B2 | 5/2014 | Zarins et al. |
| D706,432 S | 6/2014 | Martinez |
| 8,740,896 B2 | 6/2014 | Zarins et al. |
| 8,768,454 B2 | 7/2014 | Sham et al. |
| 8,768,470 B2 | 7/2014 | Deem et al. |
| 8,771,252 B2 | 7/2014 | Gelfand et al. |
| 8,774,913 B2 | 7/2014 | Demarais et al. |
| 8,774,922 B2 | 7/2014 | Zarins et al. |
| 8,775,340 B2 | 7/2014 | Waxman et al. |
| 8,784,463 B2 | 7/2014 | Zarins et al. |
| 8,785,196 B2 | 7/2014 | Kronberg et al. |
| 8,795,147 B1 | 8/2014 | Goodwin et al. |
| 8,805,521 B2 | 8/2014 | Carroll |
| 8,805,545 B2 | 8/2014 | Zarins |
| 8,818,514 B2 | 8/2014 | Zarins et al. |
| 8,827,886 B2 | 9/2014 | Chornenky et al. |
| 8,845,629 B2 | 9/2014 | Demarais et al. |
| 8,852,163 B2 | 10/2014 | Deem et al. |
| 8,880,186 B2 | 11/2014 | Levin et al. |
| 8,906,659 B2 | 12/2014 | Clyne et al. |
| 8,911,342 B2 | 12/2014 | Dissing et al. |
| 8,932,196 B2 | 1/2015 | Chornenky et al. |
| 8,934,978 B2 | 1/2015 | Deem et al. |

(56) References Cited

U.S. PATENT DOCUMENTS

| | | |
|---|---|---|
| 8,936,560 B2 | 1/2015 | Lunau et al. |
| 8,936,804 B2 | 1/2015 | Lin et al. |
| 8,948,865 B2 | 2/2015 | Zarins et al. |
| 8,958,871 B2 | 2/2015 | Demarais et al. |
| 8,961,385 B2 | 2/2015 | Pilla et al. |
| 8,968,172 B2 | 3/2015 | Wang et al. |
| 8,972,024 B2 | 3/2015 | Walker |
| 8,979,727 B2 | 3/2015 | Ron Edoute et al. |
| 8,980,851 B2 | 3/2015 | O'Connor |
| 8,983,595 B2 | 3/2015 | Levin et al. |
| 8,986,294 B2 | 3/2015 | Demarais et al. |
| 8,998,791 B2 | 4/2015 | Ron Edoute et al. |
| 9,002,477 B2 | 4/2015 | Burnett |
| 9,005,102 B2 | 4/2015 | Burnett et al. |
| 9,023,037 B2 | 5/2015 | Zarins et al. |
| 9,072,527 B2 | 7/2015 | Deem et al. |
| 9,108,040 B2 | 8/2015 | Zarins |
| 9,119,829 B2 | 9/2015 | Higgins et al. |
| 9,125,661 B2 | 9/2015 | Deem et al. |
| 9,131,978 B2 | 9/2015 | Zarins et al. |
| 9,138,281 B2 | 9/2015 | Zarins et al. |
| 9,186,198 B2 | 11/2015 | Demarais et al. |
| 9,186,213 B2 | 11/2015 | Deem et al. |
| 9,186,514 B2 | 11/2015 | Ben-Haim et al. |
| 9,192,715 B2 | 11/2015 | Gelfand et al. |
| 9,198,792 B2 | 12/2015 | Skahan et al. |
| 9,215,788 B2 | 12/2015 | Karni et al. |
| 9,232,986 B2 | 1/2016 | Scurtescu |
| 9,245,675 B2 | 1/2016 | Tsai et al. |
| 9,265,558 B2 | 2/2016 | Zarins et al. |
| 9,265,794 B2 | 2/2016 | Lin et al. |
| 9,278,231 B2 | 3/2016 | Vasishta |
| 9,289,255 B2 | 3/2016 | Deem et al. |
| 9,289,618 B1 | 3/2016 | Ben-Haim et al. |
| 9,308,043 B2 | 4/2016 | Zarins et al. |
| 9,308,044 B2 | 4/2016 | Zarins et al. |
| 9,314,363 B2 | 4/2016 | Ingimundarson et al. |
| 9,314,630 B2 | 4/2016 | Levin et al. |
| 9,320,561 B2 | 4/2016 | Zarins et al. |
| 9,320,913 B2 | 4/2016 | Dimino et al. |
| 9,321,662 B2 | 4/2016 | Holland |
| 9,326,817 B2 | 5/2016 | Zarins et al. |
| 9,327,115 B2 | 5/2016 | Neuman et al. |
| 9,327,119 B2 | 5/2016 | Skahan et al. |
| 9,327,122 B2 | 5/2016 | Zarins et al. |
| 9,327,136 B2 | 5/2016 | Hedgecock |
| 9,339,641 B2 | 5/2016 | Rajguru et al. |
| 9,345,909 B2 | 5/2016 | Feferberg |
| 9,351,790 B2 | 5/2016 | Zemel et al. |
| 9,352,002 B2 | 5/2016 | Higgins et al. |
| 9,359,233 B2 | 6/2016 | Holland |
| 9,364,267 B2 | 6/2016 | Northcutt et al. |
| 9,364,280 B2 | 6/2016 | Zarins et al. |
| 9,387,338 B2 | 7/2016 | Burnett |
| 9,387,339 B2 | 7/2016 | Sham et al. |
| 9,393,144 B2 | 7/2016 | Ingimundarson et al. |
| D762,864 S | 8/2016 | Anderson et al. |
| D763,453 S | 8/2016 | Anderson et al. |
| 9,402,992 B2 | 8/2016 | Zarins |
| 9,404,449 B2 | 8/2016 | Licitar |
| 9,411,030 B2 | 8/2016 | Weinberg |
| 9,415,233 B2 | 8/2016 | Pilla et al. |
| 9,421,357 B2 | 8/2016 | Walker |
| 9,421,370 B2 | 8/2016 | Weinstock |
| 9,427,598 B2 | 8/2016 | Pilla et al. |
| 9,433,629 B2 | 9/2016 | Paz Garcia et al. |
| 9,433,682 B2 | 9/2016 | Mohapatra et al. |
| 9,433,797 B2 | 9/2016 | Pilla et al. |
| 9,439,726 B2 | 9/2016 | Zarins et al. |
| 9,440,089 B2 | 9/2016 | Pilla et al. |
| 9,445,867 B1 | 9/2016 | Zarins et al. |
| 9,452,297 B2 | 9/2016 | Mohamed et al. |
| 9,456,869 B2 | 10/2016 | Zarins et al. |
| 9,463,066 B2 | 10/2016 | Deem et al. |
| 9,468,497 B2 | 10/2016 | Zarins et al. |
| 9,474,563 B2 | 10/2016 | Zarins et al. |
| 9,480,991 B2 | 11/2016 | Baym et al. |
| 9,486,270 B2 | 11/2016 | Zarins et al. |
| 9,486,638 B2 | 11/2016 | Chornenky et al. |
| 9,498,491 B2 | 11/2016 | Black, Sr. |
| 9,498,638 B2 | 11/2016 | Ruetenik |
| 9,498,639 B2 | 11/2016 | Anderson et al. |
| 9,510,931 B2 | 12/2016 | Hotter et al. |
| 9,526,918 B2 | 12/2016 | Kruip |
| 9,532,832 B2 | 1/2017 | Ron Edoute et al. |
| 9,554,935 B2 | 1/2017 | Ingimundarson et al. |
| 9,556,243 B2 | 1/2017 | Leach et al. |
| 9,603,637 B2 | 3/2017 | Northcutt et al. |
| 9,610,443 B1 | 4/2017 | Dean et al. |
| 9,610,459 B2 | 4/2017 | Burnett et al. |
| 9,612,308 B2 | 4/2017 | Weinberg et al. |
| 9,630,001 B2 | 4/2017 | Kronberg et al. |
| 9,630,004 B2 | 4/2017 | Rajguru et al. |
| 9,636,174 B2 | 5/2017 | Zarins et al. |
| 9,656,096 B2 | 5/2017 | Pilla |
| 9,662,183 B2 | 5/2017 | Lowe et al. |
| 9,669,074 B2 | 6/2017 | Paz Garcia et al. |
| 9,675,413 B2 | 6/2017 | Deem et al. |
| 9,684,074 B2 | 6/2017 | Schrank et al. |
| 9,694,193 B2 | 7/2017 | Van Bree et al. |
| 9,694,194 B2 | 7/2017 | Ron Edoute et al. |
| 9,707,035 B2 | 7/2017 | Zarins et al. |
| 9,724,308 B2 | 8/2017 | Paukshto et al. |
| 9,724,534 B2 | 8/2017 | Jacobson et al. |
| 9,726,738 B2 | 8/2017 | Weinberg et al. |
| 9,727,764 B2 | 8/2017 | Hassler et al. |
| 9,730,946 B2 | 8/2017 | Lin et al. |
| 9,731,132 B2 | 8/2017 | Deem et al. |
| 9,735,629 B2 | 8/2017 | Wagman et al. |
| 9,743,983 B2 | 8/2017 | Levin et al. |
| 9,746,407 B2 | 8/2017 | Bernardi et al. |
| 9,757,192 B2 | 9/2017 | Levin et al. |
| 9,757,193 B2 | 9/2017 | Zarins et al. |
| 9,757,583 B2 | 9/2017 | Mohamed et al. |
| 9,757,584 B2 | 9/2017 | Burnett |
| 9,758,806 B2 | 9/2017 | Woodell-May et al. |
| 9,776,014 B2 | 10/2017 | Neuman et al. |
| 9,795,500 B2 | 10/2017 | Ingimundarson et al. |
| 9,796,609 B2 | 10/2017 | Holland |
| 9,801,905 B2 | 10/2017 | Mohamed et al. |
| 2001/0007937 A1 | 7/2001 | MacKin |
| 2001/0027278 A1 | 10/2001 | Kaufman et al. |
| 2001/0031906 A1 | 10/2001 | Ishikawa et al. |
| 2001/0031986 A1 | 10/2001 | Hauck |
| 2001/0041820 A1 | 11/2001 | Woo |
| 2001/0044643 A1 | 11/2001 | Litovitz |
| 2002/0022863 A1 | 2/2002 | Hauck |
| 2002/0034796 A1 | 3/2002 | Shastri et al. |
| 2002/0035358 A1 | 3/2002 | Wang |
| 2002/0052634 A1 | 5/2002 | March |
| 2002/0086842 A1 | 7/2002 | Plank et al. |
| 2002/0091850 A1 | 7/2002 | Perholtz et al. |
| 2002/0147380 A1 | 10/2002 | Ardizzone |
| 2002/0165583 A1 | 11/2002 | Tepper et al. |
| 2003/0018368 A1 | 1/2003 | Ansarinia |
| 2003/0023283 A1 | 1/2003 | McDaniel |
| 2003/0028072 A1 | 2/2003 | Fischell et al. |
| 2003/0050527 A1 | 3/2003 | Fox et al. |
| 2003/0083537 A1 | 5/2003 | Ardizzone |
| 2003/0093028 A1 | 5/2003 | Spiegel |
| 2003/0095022 A1 | 5/2003 | Boynton et al. |
| 2003/0099979 A1 | 5/2003 | Ohtani et al. |
| 2003/0125661 A1 | 7/2003 | Yerushalmy |
| 2003/0125769 A1 | 7/2003 | Brighton |
| 2003/0130709 A1 | 7/2003 | D.C. et al. |
| 2003/0158583 A1 | 8/2003 | Burnett et al. |
| 2003/0158585 A1 | 8/2003 | Burnett |
| 2003/0163168 A1 | 8/2003 | Hauck |
| 2003/0171640 A1 | 9/2003 | Canedo |
| 2003/0176895 A1 | 9/2003 | Hauck |
| 2003/0181791 A1 | 9/2003 | Thomas et al. |
| 2003/0195594 A1 | 10/2003 | Litovitz |
| 2003/0211084 A1 | 11/2003 | Brighton et al. |
| 2004/0005297 A1 | 1/2004 | Connelly et al. |

(56) References Cited

U.S. PATENT DOCUMENTS

| | | |
|---|---|---|
| 2004/0006373 A1 | 1/2004 | Brighton et al. |
| 2004/0054379 A1 | 3/2004 | Carroll et al. |
| 2004/0073260 A1 | 4/2004 | Brighton |
| 2004/0073269 A1 | 4/2004 | Carroll et al. |
| 2004/0077923 A1 | 4/2004 | Frimerman et al. |
| 2004/0106843 A1 | 6/2004 | Ardizzone et al. |
| 2004/0122281 A1 | 6/2004 | Fischell et al. |
| 2004/0138709 A1 | 7/2004 | Brighton |
| 2004/0138722 A1 | 7/2004 | Carroll et al. |
| 2004/0176803 A1 | 9/2004 | Whelan et al. |
| 2004/0176805 A1 | 9/2004 | Whelan et al. |
| 2004/0176806 A1 | 9/2004 | Markoll |
| 2004/0210254 A1 | 10/2004 | Burnett et al. |
| 2004/0230224 A1 | 11/2004 | Gordon |
| 2004/0241311 A1 | 12/2004 | Baianu et al. |
| 2004/0267333 A1 | 12/2004 | Kronberg |
| 2005/0005120 A1 | 1/2005 | Kahn et al. |
| 2005/0049640 A1 | 3/2005 | Gurtner et al. |
| 2005/0059153 A1 | 3/2005 | George et al. |
| 2005/0065394 A1 | 3/2005 | Spiegel |
| 2005/0084962 A1 | 4/2005 | Simon |
| 2005/0124847 A1 | 6/2005 | Ardizzone et al. |
| 2005/0134265 A1 | 6/2005 | Watkins et al. |
| 2005/0148807 A1 | 7/2005 | Salkinder et al. |
| 2005/0154426 A1 | 7/2005 | Boveja et al. |
| 2005/0165460 A1 | 7/2005 | Erfan |
| 2005/0177203 A1 | 8/2005 | Brighton et al. |
| 2005/0182287 A1 | 8/2005 | Becker |
| 2005/0187423 A1 | 8/2005 | Ardizzone et al. |
| 2005/0197522 A1 | 9/2005 | Pilla |
| 2005/0198812 A1 | 9/2005 | Schuster et al. |
| 2005/0215842 A1 | 9/2005 | Pilla et al. |
| 2005/0222625 A1 | 10/2005 | Laniado et al. |
| 2005/0228209 A1 | 10/2005 | Schneider et al. |
| 2005/0251229 A1 | 11/2005 | Pilla et al. |
| 2005/0259373 A1 | 11/2005 | Hoopes |
| 2005/0267355 A1 | 12/2005 | Parker |
| 2005/0288744 A1 | 12/2005 | Pilla et al. |
| 2006/0009825 A1 | 1/2006 | Chiriaev et al. |
| 2006/0024822 A1 | 2/2006 | Chang et al. |
| 2006/0030896 A1 | 2/2006 | Simon et al. |
| 2006/0030906 A1 | 2/2006 | Carroll |
| 2006/0051328 A1 | 3/2006 | Johnson |
| 2006/0057693 A1 | 3/2006 | Simon |
| 2006/0085049 A1 | 4/2006 | Cory et al. |
| 2006/0094112 A1 | 5/2006 | Babalola et al. |
| 2006/0094924 A1 | 5/2006 | Riehl |
| 2006/0129022 A1 | 6/2006 | Venza et al. |
| 2006/0161226 A1 | 7/2006 | McMickle |
| 2006/0190043 A1 | 8/2006 | Brighton et al. |
| 2006/0205993 A1 | 9/2006 | Fischell et al. |
| 2006/0206174 A1 | 9/2006 | Honeycutt et al. |
| 2006/0212077 A1 | 9/2006 | Pilla et al. |
| 2006/0235473 A1 | 10/2006 | Brighton |
| 2006/0240316 A1 | 10/2006 | Martinez |
| 2006/0245217 A1 | 11/2006 | Kirbie et al. |
| 2006/0258896 A1 | 11/2006 | Haber et al. |
| 2006/0271131 A1 | 11/2006 | Passy et al. |
| 2006/0293724 A1 | 12/2006 | Kronberg et al. |
| 2007/0014055 A1 | 1/2007 | Ness |
| 2007/0021645 A1 | 1/2007 | Zimmerman |
| 2007/0026514 A1 | 2/2007 | Pilla et al. |
| 2007/0027355 A1 | 2/2007 | Riehl et al. |
| 2007/0030176 A1 | 2/2007 | Sanchez-Olea et al. |
| 2007/0038252 A1 | 2/2007 | Carroll |
| 2007/0039211 A1 | 2/2007 | Pichler |
| 2007/0043254 A1 | 2/2007 | DeMarco |
| 2007/0060477 A1 | 3/2007 | Pedersen et al. |
| 2007/0060954 A1 | 3/2007 | Cameron et al. |
| 2007/0060981 A1 | 3/2007 | Pille et al. |
| 2007/0065420 A1 | 3/2007 | Johnson |
| 2007/0078292 A1 | 4/2007 | Markov et al. |
| 2007/0104694 A1 | 5/2007 | Quijano et al. |
| 2007/0105769 A1 | 5/2007 | Simon |
| 2007/0139167 A1 | 6/2007 | Gilson et al. |
| 2007/0149901 A1 | 6/2007 | Gordon et al. |
| 2007/0173904 A1 | 7/2007 | Pilla |
| 2007/0203389 A1 | 8/2007 | Bergman |
| 2007/0203390 A1 | 8/2007 | Rohan et al. |
| 2007/0208249 A1 | 9/2007 | Kumar |
| 2007/0208385 A1 | 9/2007 | Carroll et al. |
| 2007/0212538 A1 | 9/2007 | Niu |
| 2007/0282156 A1 | 12/2007 | Konings |
| 2007/0288072 A1 | 12/2007 | Pascual-Leone et al. |
| 2007/0299472 A1 | 12/2007 | Brighton |
| 2008/0015463 A1 | 1/2008 | Goldstein |
| 2008/0021327 A1 | 1/2008 | El-Bialy et al. |
| 2008/0039901 A1 | 2/2008 | Kronberg et al. |
| 2008/0058793 A1 | 3/2008 | Pilla et al. |
| 2008/0077193 A1 | 3/2008 | Bow et al. |
| 2008/0092435 A1 | 4/2008 | Bzdek et al. |
| 2008/0097142 A1 | 4/2008 | Savage |
| 2008/0125617 A1 | 5/2008 | Puchek |
| 2008/0132971 A1 | 6/2008 | Pille et al. |
| 2008/0140155 A1 | 6/2008 | Pilla et al. |
| 2008/0200749 A1 | 8/2008 | Zheng et al. |
| 2008/0208284 A1 | 8/2008 | Rezai et al. |
| 2008/0208287 A1 | 8/2008 | Palermo et al. |
| 2008/0215113 A1 | 9/2008 | Pawlowicz |
| 2008/0215116 A1 | 9/2008 | Brighton |
| 2008/0217263 A1 | 9/2008 | Higgins et al. |
| 2008/0228185 A1 | 9/2008 | Vasta et al. |
| 2008/0269838 A1 | 10/2008 | Brighton et al. |
| 2008/0280169 A1 | 11/2008 | Niu et al. |
| 2008/0280826 A1 | 11/2008 | O'Connor |
| 2008/0287730 A1 | 11/2008 | Spiegel |
| 2008/0288035 A1 | 11/2008 | Gill et al. |
| 2008/0294269 A1 | 11/2008 | Fell |
| 2008/0306325 A1 | 12/2008 | Burnett et al. |
| 2009/0018613 A1 | 1/2009 | Brighton |
| 2009/0030476 A1 | 1/2009 | Hargrove |
| 2009/0043188 A1 | 2/2009 | Rauscher |
| 2009/0062885 A1 | 3/2009 | Brighton et al. |
| 2009/0099623 A1 | 4/2009 | Bentwich |
| 2009/0104160 A1 | 4/2009 | Young et al. |
| 2009/0105781 A1 | 4/2009 | Brighton |
| 2009/0131739 A1 | 5/2009 | Shalev |
| 2009/0132010 A1 | 5/2009 | Kronberg |
| 2009/0156884 A1 | 6/2009 | Schneider et al. |
| 2009/0163762 A1 | 6/2009 | Setti et al. |
| 2009/0206882 A1 | 8/2009 | Patterson |
| 2009/0206883 A1 | 8/2009 | Patterson |
| 2009/0206907 A1 | 8/2009 | Patterson |
| 2009/0216068 A1 | 8/2009 | Thomas et al. |
| 2009/0227829 A1 | 9/2009 | Burnett et al. |
| 2009/0227831 A1 | 9/2009 | Burnett et al. |
| 2009/0234179 A1 | 9/2009 | Burnett et al. |
| 2009/0234417 A1 | 9/2009 | Pastena et al. |
| 2009/0240310 A1 | 9/2009 | Kennedy |
| 2009/0287126 A1 | 11/2009 | Skahan et al. |
| 2009/0326315 A1 | 12/2009 | Nishi et al. |
| 2009/0326602 A1 | 12/2009 | Glukhovsky et al. |
| 2010/0004500 A1 | 1/2010 | Gliner et al. |
| 2010/0005571 A1 | 1/2010 | Moss et al. |
| 2010/0010288 A1 | 1/2010 | Von Ohlsen et al. |
| 2010/0049262 A1 | 2/2010 | Puchek |
| 2010/0057655 A1 | 3/2010 | Jacobson et al. |
| 2010/0075211 A1 | 3/2010 | Martinez |
| 2010/0082079 A1 | 4/2010 | Skahan et al. |
| 2010/0121407 A1 | 5/2010 | Pfaff et al. |
| 2010/0160712 A1 | 6/2010 | Burnett et al. |
| 2010/0160999 A1 | 6/2010 | Epstein et al. |
| 2010/0168501 A1 | 7/2010 | Burnett et al. |
| 2010/0179373 A1 | 7/2010 | Pille et al. |
| 2010/0185041 A1 | 7/2010 | Lee |
| 2010/0197993 A1 | 8/2010 | Vasishta |
| 2010/0204538 A1 | 8/2010 | Burnett et al. |
| 2010/0210893 A1 | 8/2010 | Pilla |
| 2010/0221346 A1 | 9/2010 | Plank et al. |
| 2010/0222629 A1 | 9/2010 | Burnett et al. |
| 2010/0222631 A1 | 9/2010 | Pilla |
| 2010/0239544 A1 | 9/2010 | Simon |
| 2010/0262052 A1 | 10/2010 | Lunau et al. |
| 2010/0298624 A1 | 11/2010 | Becker |

(56) References Cited

U.S. PATENT DOCUMENTS

| | | |
|---|---|---|
| 2011/0004261 A1 | 1/2011 | Sham et al. |
| 2011/0021863 A1 | 1/2011 | Burnett et al. |
| 2011/0065976 A1 | 3/2011 | Chornenky et al. |
| 2011/0065977 A1 | 3/2011 | Sham et al. |
| 2011/0105959 A1 | 5/2011 | O'Connor |
| 2011/0112352 A1 | 5/2011 | Pilla et al. |
| 2011/0112522 A1 | 5/2011 | Wetling |
| 2011/0118852 A1 | 5/2011 | Evans |
| 2011/0124717 A1 | 5/2011 | O'Connor |
| 2011/0130618 A1 | 6/2011 | Ron Edoute et al. |
| 2011/0152598 A1 | 6/2011 | Pilla et al. |
| 2011/0160811 A1 | 6/2011 | Walker |
| 2011/0184223 A1 | 7/2011 | Peterchev et al. |
| 2011/0190849 A1 | 8/2011 | Faltys et al. |
| 2011/0207989 A1 | 8/2011 | Pilla et al. |
| 2011/0213195 A1 | 9/2011 | Kraus et al. |
| 2011/0217775 A1 | 9/2011 | Kronberg et al. |
| 2011/0224480 A1 | 9/2011 | Weinstock |
| 2011/0282412 A1 | 11/2011 | Glukhovsky et al. |
| 2011/0288611 A1 | 11/2011 | Lunau et al. |
| 2011/0295339 A1 | 12/2011 | Carroll |
| 2012/0016442 A1 | 1/2012 | Brighton et al. |
| 2012/0038441 A1 | 2/2012 | Wilson et al. |
| 2012/0059287 A1 | 3/2012 | El-Bialy et al. |
| 2012/0078328 A1 | 3/2012 | Vancraeyenest et al. |
| 2012/0089201 A1 | 4/2012 | Pilla |
| 2012/0101327 A1 | 4/2012 | Dissing et al. |
| 2012/0101544 A1 | 4/2012 | Hoberman et al. |
| 2012/0116149 A1 | 5/2012 | Pilla et al. |
| 2012/0135390 A1 | 5/2012 | Clyne et al. |
| 2012/0135392 A1 | 5/2012 | El-Bialy et al. |
| 2012/0143285 A1 | 6/2012 | Wang et al. |
| 2012/0149968 A1 | 6/2012 | Brighton |
| 2012/0172653 A1 | 7/2012 | Chornenky et al. |
| 2012/0184800 A1 | 7/2012 | Brighton |
| 2012/0215281 A1 | 8/2012 | Neuman |
| 2012/0245403 A1 | 9/2012 | Martinez |
| 2012/0253101 A1 | 10/2012 | Wang et al. |
| 2012/0265048 A1 | 10/2012 | Biggs et al. |
| 2012/0302821 A1 | 11/2012 | Burnett |
| 2012/0316482 A1 | 12/2012 | Karim |
| 2012/0330090 A1 | 12/2012 | Sham et al. |
| 2013/0013339 A1 | 1/2013 | Goldman et al. |
| 2013/0035539 A1 | 2/2013 | Kornstein |
| 2013/0066392 A1* | 3/2013 | Simon .................. A61N 1/40 607/45 |
| 2013/0072746 A1 | 3/2013 | Burnett et al. |
| 2013/0085317 A1 | 4/2013 | Feinstein |
| 2013/0158456 A1 | 6/2013 | Skahan et al. |
| 2013/0158634 A1 | 6/2013 | Ron Edoute et al. |
| 2013/0165829 A1 | 6/2013 | Carroll |
| 2013/0171094 A1 | 7/2013 | Lin et al. |
| 2013/0178425 A1 | 7/2013 | Higgins et al. |
| 2013/0218235 A9 | 8/2013 | Pilla et al. |
| 2013/0238061 A1 | 9/2013 | Ron Edoute et al. |
| 2013/0238062 A1 | 9/2013 | Ron Edoute et al. |
| 2013/0245358 A1 | 9/2013 | Johnson et al. |
| 2013/0261374 A1 | 10/2013 | Elder |
| 2013/0267003 A1 | 10/2013 | Goodwin et al. |
| 2013/0267020 A1 | 10/2013 | Goodwin et al. |
| 2013/0274540 A1 | 10/2013 | Pilla et al. |
| 2013/0288260 A1 | 10/2013 | Rubin et al. |
| 2013/0289416 A1 | 10/2013 | Feferberg |
| 2013/0293327 A1 | 11/2013 | Wilson et al. |
| 2013/0296940 A1 | 11/2013 | Northcutt et al. |
| 2013/0317282 A1 | 11/2013 | Ron Edoute et al. |
| 2013/0344559 A1 | 12/2013 | Engeberg et al. |
| 2014/0023983 A1 | 1/2014 | Lowe et al. |
| 2014/0024882 A1 | 1/2014 | Chornenky et al. |
| 2014/0046115 A1 | 2/2014 | Pilla |
| 2014/0046117 A1 | 2/2014 | Pilla |
| 2014/0046232 A1 | 2/2014 | Sham et al. |
| 2014/0046423 A1 | 2/2014 | Rajguru et al. |
| 2014/0066837 A1 | 3/2014 | Moy |
| 2014/0081070 A1 | 3/2014 | Paukshto et al. |
| 2014/0114382 A1 | 4/2014 | Kim |
| 2014/0148870 A1 | 5/2014 | Burnett |
| 2014/0155799 A1 | 6/2014 | Skahan et al. |
| 2014/0163304 A1 | 6/2014 | Burnett et al. |
| 2014/0207018 A1 | 7/2014 | Weinstock |
| 2014/0207040 A1 | 7/2014 | Ingimundarson et al. |
| 2014/0207041 A1 | 7/2014 | Ingimundarson et al. |
| 2014/0213843 A1 | 7/2014 | Pilla et al. |
| 2014/0213844 A1 | 7/2014 | Pilla et al. |
| 2014/0221726 A1 | 8/2014 | Pilla et al. |
| 2014/0228620 A1 | 8/2014 | Vasishta |
| 2014/0249354 A1 | 9/2014 | Anderson et al. |
| 2014/0249355 A1 | 9/2014 | Martinez |
| 2014/0303425 A1 | 10/2014 | Pilla et al. |
| 2014/0322292 A1 | 10/2014 | Lin et al. |
| 2014/0342300 A1 | 11/2014 | Schnaitter |
| 2014/0342428 A1 | 11/2014 | Goodwin et al. |
| 2014/0343642 A1 | 11/2014 | Lauer |
| 2014/0350649 A1 | 11/2014 | Kronberg et al. |
| 2015/0005672 A1 | 1/2015 | Gangwish et al. |
| 2015/0010499 A1 | 1/2015 | Lin et al. |
| 2015/0025299 A1 | 1/2015 | Ron Edoute et al. |
| 2015/0094521 A1 | 4/2015 | Neuman et al. |
| 2015/0099804 A1 | 4/2015 | Lin et al. |
| 2015/0107774 A1 | 4/2015 | Lee |
| 2015/0141736 A1 | 5/2015 | Tsai et al. |
| 2015/0151136 A1 | 6/2015 | Ruetenik |
| 2015/0174166 A1 | 6/2015 | Giampapa |
| 2015/0196771 A1 | 7/2015 | Pilla et al. |
| 2015/0202454 A1 | 7/2015 | Burnett |
| 2015/0217107 A1 | 8/2015 | Walker |
| 2015/0217125 A1 | 8/2015 | Chornenky et al. |
| 2015/0217126 A1 | 8/2015 | Pilla |
| 2015/0258346 A1 | 9/2015 | Cadossi et al. |
| 2015/0273221 A1 | 10/2015 | Manning et al. |
| 2015/0297910 A1 | 10/2015 | Dimino et al. |
| 2015/0306412 A1 | 10/2015 | Durschmidt |
| 2015/0315539 A1 | 11/2015 | Villanueva et al. |
| 2015/0320697 A1 | 11/2015 | O'Connor |
| 2015/0328033 A1 | 11/2015 | Ingimundarson et al. |
| 2015/0328034 A1 | 11/2015 | Ingimundarson et al. |
| 2015/0328476 A1 | 11/2015 | Anderson et al. |
| 2015/0342661 A1 | 12/2015 | Ron Edoute |
| 2016/0000870 A1 | 1/2016 | Higgins et al. |
| 2016/0008024 A1 | 1/2016 | Payne et al. |
| 2016/0015432 A1 | 1/2016 | Northcutt et al. |
| 2016/0015545 A1 | 1/2016 | Petursson |
| 2016/0022989 A1 | 1/2016 | Pfeifer |
| 2016/0038753 A1 | 2/2016 | Chornenky et al. |
| 2016/0051827 A1 | 2/2016 | Ron Edoute et al. |
| 2016/0067103 A1 | 3/2016 | Anthony |
| 2016/0067497 A1* | 3/2016 | Levine ............... A61B 5/6877 607/62 |
| 2016/0067515 A1 | 3/2016 | Burnett et al. |
| 2016/0067517 A1 | 3/2016 | Burnett |
| 2016/0074670 A1 | 3/2016 | Mohamed et al. |
| 2016/0074671 A1 | 3/2016 | Burnett et al. |
| 2016/0121135 A1 | 5/2016 | Pilla |
| 2016/0129273 A1 | 5/2016 | Park |
| 2016/0129274 A1 | 5/2016 | Park |
| 2016/0129284 A1 | 5/2016 | Mikus |
| 2016/0145571 A1 | 5/2016 | Giampapa |
| 2016/0151416 A1 | 6/2016 | Lin et al. |
| 2016/0151646 A1 | 6/2016 | Bonutti et al. |
| 2016/0193466 A1 | 7/2016 | Burnett |
| 2016/0206876 A1 | 7/2016 | Rajguru et al. |
| 2016/0228721 A1 | 8/2016 | Mohamed et al. |
| 2016/0228723 A1 | 8/2016 | Mohamed et al. |
| 2016/0235983 A1 | 8/2016 | Berman et al. |
| 2016/0246944 A1 | 8/2016 | Jain et al. |
| 2016/0306042 A1 | 10/2016 | Schrank et al. |
| 2016/0313159 A1 | 10/2016 | Appel et al. |
| 2016/0317828 A1 | 11/2016 | Sham et al. |
| 2016/0331990 A1 | 11/2016 | Mohamed et al. |
| 2016/0339261 A1 | 11/2016 | Mletzko |
| 2016/0346016 A1 | 12/2016 | Northcutt |
| 2016/0346561 A1 | 12/2016 | Ron Edoute et al. |
| 2016/0354446 A1 | 12/2016 | Paz Garcia et al. |
| 2016/0372362 A1 | 12/2016 | Signamarcheix et al. |

(56) References Cited

U.S. PATENT DOCUMENTS

| | | |
|---|---|---|
| 2017/0000536 A1 | 1/2017 | Tacktill |
| 2017/0001025 A1 | 1/2017 | Schwarz et al. |
| 2017/0001201 A1 | 1/2017 | Baym et al. |
| 2017/0027858 A1 | 2/2017 | Borgens et al. |
| 2017/0028184 A1 | 2/2017 | Godden et al. |
| 2017/0030188 A1 | 2/2017 | Lehr |
| 2017/0039404 A1 | 2/2017 | Hassler et al. |
| 2017/0043177 A1 | 2/2017 | Ron Edoute et al. |
| 2017/0050019 A1 | 2/2017 | Ron Edoute et al. |
| 2017/0056644 A1 | 3/2017 | Chahine et al. |
| 2017/0071977 A1 | 3/2017 | Mohamed et al. |
| 2017/0072210 A1 | 3/2017 | Gangwish et al. |
| 2017/0080245 A1 | 3/2017 | Dimino et al. |
| 2017/0087367 A1 | 3/2017 | Weisend |
| 2017/0113059 A1 | 4/2017 | Fisher |
| 2017/0113060 A1 | 4/2017 | Anderson et al. |
| 2017/0128538 A1 | 5/2017 | Toler et al. |
| 2017/0151442 A1 | 6/2017 | Walborn |
| 2017/0152500 A1 | 6/2017 | Seo et al. |
| 2017/0157318 A1 | 6/2017 | Balakrishnan |
| 2017/0165496 A1 | 6/2017 | Pilla et al. |
| 2017/0173076 A1 | 6/2017 | Greco et al. |
| 2017/0173295 A1 | 6/2017 | Sanderson et al. |
| 2017/0173347 A1 | 6/2017 | Schwarz et al. |
| 2017/0202509 A1 | 7/2017 | Sanderson et al. |
| 2017/0209717 A1 | 7/2017 | Bonutti et al. |
| 2017/0225005 A1 | 8/2017 | Burnett et al. |
| 2017/0226463 A1 | 8/2017 | Kronberg et al. |
| 2017/0246481 A1 | 8/2017 | Mishelevich |
| 2017/0252574 A1 | 9/2017 | Cabrerizo et al. |
| 2017/0266443 A1 | 9/2017 | Rajguru et al. |
| 2017/0266458 A1 | 9/2017 | Pilla |
| 2017/0266459 A1 | 9/2017 | Mohamed et al. |
| 2017/0291039 A1 | 10/2017 | Jacobson et al. |
| 2017/0295778 A1 | 10/2017 | Ales et al. |
| 2017/0298340 A1 | 10/2017 | Goodwin et al. |
| 2017/0298341 A1 | 10/2017 | Goodwin et al. |
| 2017/0304642 A1 | 10/2017 | Ron Edoute et al. |
| 2017/0319250 A1 | 11/2017 | Whittaker et al. |

FOREIGN PATENT DOCUMENTS

| | | |
|---|---|---|
| RU | 94025257 | 5/1996 |
| RU | 2248229 | 3/2005 |
| WO | WO8301742 | 5/1983 |
| WO | WO9527533 | 10/1995 |
| WO | WO9611723 | 4/1996 |
| WO | WO9632158 | 10/1996 |
| WO | WO0115774 | 3/2001 |
| WO | WO0209811 | 2/2002 |
| WO | WO2004108208 | 12/2004 |
| WO | WO2005051306 | 6/2005 |
| WO | WO2008070001 | 6/2008 |
| WO | WO2009155516 | 12/2009 |
| WO | WO2010067336 | 6/2010 |
| WO | WO2010149164 | 12/2010 |
| WO | WO2011053607 | 5/2011 |

* cited by examiner

SYSTEM AND METHOD FOR APPLYING A LOW FREQUENCY MAGNETIC FIELD TO BIOLOGICAL TISSUES

CROSS REFERENCE TO RELATED APPLICATIONS

The present application claims benefit of priority from, and is a non-provisional of, U.S. Provisional Patent Application No. 62/420,337, filed Nov. 10, 2016, the entirety of which is expressly incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

1. Field of the Invention

This invention pertains to a system and method for providing a therapeutic magnetic field at a frequency of about 5 Hz-50 kHz.

2. Discussion of Related Art

It is now well established that application of weak non-thermal electromagnetic fields ("EMF") can result in physiologically meaningful in vivo and in vitro bioeffects. Time-varying electromagnetic fields, comprising rectangular waveforms such as pulsing electromagnetic fields ("PEMF"), and sinusoidal waveforms such as pulsed radio frequency fields ("PRF") ranging from several Hertz, are clinically beneficial when used as an adjunctive therapy for a variety of musculoskeletal injuries and conditions.

Wade, Brett, "A Review of Pulsed Electromagnetic Field (PEMF) Mechanisms at a Cellular Level: A Rationale for Clinical Use", American Journal of Health Research. Vol. 1, No. 3, 2013, pp. 51-55. doi: 10.11648/j.ajhr.20130103.13, also discusses various PEMF studies. Significant tissue healing effects, particularly with the modality PEMF, are likely the result of increased activity in non-excitable cells. Electromagnetic modalities include any modality which uses electricity and therefore generates both an electric field and a magnetic field. In physiotherapy practice, these electromagnetic modalities are generally used to expedite recovery of soft tissue injuries or alleviate pain. The movement of the electrons will cause ions to move towards the electrodes and thereby, ostensibly, affecting the physiology of the cell. Ions such as calcium ($Ca^{2+}$), potassium ($K^+$), sodium ($Na^+$), chlorine ($Cl^-$), etc. Ions have numerous roles in the cellular physiology of cells. The movement of ions through ion channels in the plasma membrane and organelles have important roles in excitable and non-excitable cells such as nerve cell signal propagation, muscle contractions, energy production, etc. Electrotherapy education has traditionally attributed the positive effects of electrotherapy to the effects of an electric current causing a depolarization of excitable cells by the forced movement of ions ($Na^+$ and $K^+$) across the plasma membrane.

As previously described, negatively anions such as $Cl^-$ will, in theory, be attracted to the positive charge of the externally applied electrode and positively charged ions such as $Na^+$ and K+ will be attracted to the negative electrode. If the current used is a simple direct current (electrons flowing only in one direction), there would be build-up of same-charge ions concentrating in one area. This would have a significant effect on local pH due to increased concentrations of hydrochloric acid and sodium hydroxide leading to cause pain and cellular damage. Therefore, electrotherapy is usually the use of a direct current that is both pulsed and bi-directional to prevent excessive build-up of ions under an electrode. A paper published by Panagopoulos et al. (3) suggested a hypothesis whereby the externally applied electromagnetic field causes the ions to vibrate and when this vibration reaches a critical point, this gives a false signal to the voltage gated channels present in the membranes of eukaryotic cells. Once the channel receives a false signal, the gate may be forced to either open or perhaps close but theoretically affecting the physiology of the cell.

Panagopoulos et al. further describe how both the oscillating electric and magnetic fields can have similar effects on the free ions and consequently the voltage gated channels. It has long been argued that low frequency; non-ionizing radiation has no significant bioactive effects on cells. This, in fact, has been the argument for why wireless technology and the use of cellular telephones should have no negative effects to human health. The theory presented by Panagopoulos et al. suggests that, because of the inverse relationship between amplitude of the "ion's forced vibration" and frequency, lower frequency electromagnetic fields have the potential to be more bioactive. The authors provide a mathematical model which also explains how pulsed fields (on for a period and off for a period) are more bioactive than static fields of the same parameters, and their calculations demonstrate how either pulsed electromagnetic fields or the time of onset or removal of an external field will be twice as active as non-pulsatile fields. The calculations support other observations which have found bioactive effects with pulsed fields of extremely low frequency.

While any of the electromagnetic modalities can theoretically attribute their effects to both the electric and magnetic field, only PEMF is designed specifically to direct magnetic fields through the tissues to facilitate healing. The purported mechanism of action of magnetic fields on cells is has been suggested by Panagopoulos et al. Another paper by Ganesan et al. (4) reviewed the literature for PEMF in the treatment of arthritis. In addition to the effects suggested by Panagopoulos et al., Ganesan et al., suggest that $Ca^{2+}$ may be modulated by the externally applied magnetic field which in turn could affect many important voltage gated aspects of cell physiology including gene activation, signal transduction, cAMP production, immune function, etc. Looking specifically at the effects of a pulsed magnetic field related to arthritis, Ganesan et al., review research which has found increased chondrocyte production in joints exposed to PEMF. The authors also review research which demonstrates a decrease in pro-inflammatory cytokines such as TNF-alpha and IL-6. In vitro studies have also demonstrated that PEMF has significant effects on both excitable and non-excitable cells leading to osteogenesis (5) and chondrocyte proliferation (6). The research into positive effects with PEMF and multiple sclerosis (MS) has found beneficial effects from PEMF using much weaker intensities (7). Sandyk has shown positive results with MS in the picotesla intensities (8).

If the electric field is created by a movement of electrons, the resultant magnetic field is also capable of inducing electric currents in a surrounding medium. The magnetic field created by the moving electrons is essentially a field of virtual photons creating force lines. This magnetic field is capable of causing movement of particles with an electric charge such as ions. This force is known as a Lorentz force. Since PEMF is not using an electric field per se, there is no electron flow with frequency and pulse width suitable for stimulating sensory or motor nerves. What the electric field and the magnetic field have in common is the forced movement of ions. If an externally applied electromagnetic field can cause the forced movement of ions across a plasma membrane and we know that these movements can affect cellular physiology, are there "windows" of frequency and intensity which may be more effective? The parameters which have shown to be the most effective with PEMF in treating pathologies such as: bone healing, wound healing, ligament healing, and cartilage-healing range from 15-75 Hz and use intensities in the militesla range. Markov (9) has suggested "three amplitude windows" with PEMF: 50-100 µT, 15-20 mT, and 45-50 mT. Summarized below are some of the effects on non-excitable cells exposed to PEMF.
Cells Mechanism, PEMF parameters, References
Chondrocytes Increased number of chondrocytes 75 Hz, 2.3 mT (Murray 1985)
Osteoblasts Increased proliferation of osteoblasts 15 Hz, 0.1 mT (Marino 1970)
Osteoclasts Decreased production of osteoclasts 7.5 Hz, 300 µs,
Neutrophils Saturates adenosine receptors leading to dec. inflammatory cytokine cascade 75 Hz, 0.2 mT-3.5 mT (Doillon 1987)
Mononuclear Significant inc. IL-1β & TNF-α (Pro inf. cytokines) 50 Hz, 2.25 mT (Doillon 1986)
Fibroblasts Red. cAMP leads to inc. proliferation of collagen cells 15 Hz, 4.8 ms pulse (Basset 1981)
Endothelial Inc. proliferation of endothelial cells leading to angiogenesis. 50 Hz, 1 mT (Brighton 1981)

In general, the PEMF mats use frequencies that range from 5-300 Hz which is generally classified in a range of electromagnetic frequencies known as extremely low frequency (ELF). The magnetic field intensities used by these machines are usually in the micro and millitesla range.

The research to date has shown that the mechanisms by which PEMF works are complicated and likely involve many pathways. It is clear that certain windows of frequency and intensity are capable of increasing mitosis in cells such as chondrocytes, osteoblasts, fibrocytes and endothelial cells. These effects will lead to improved healing time of soft tissues and bone. In addition to increasing cell metabolism, perhaps PEMF's greatest power is in its ability to ameliorate the effects of inflammation by decreasing inflammatory cytokines. This effect should give the practitioner cause to consider PEMF in the treatment of numerous inflammatory conditions including, perhaps, autoimmune diseases such as MS. It is also conceivable, as suggested by Gordon (2007), that another important effect of PEMF is the ability of the magnetic fields to restore "equilibrium in ROS (free radical)/antioxidant chemistry. Gordon (2007) explains that since both reactive oxygen species (ROS) free radicals such as superoxide anion (O.) and hydroxyl anion (OH.) are paramagnetic, they will be affected by a magnetic field. This forced vibration (similar to the effect on ions such as $K^+$, $Na^+$, $Cl^-$, $Ca^{2+}$) is thought to enhance the homeostasis between ROS and antioxidants. It is unequivocal that all chronic diseases result from a lack of homeostasis between free radicals and antioxidants. While both free radicals and antioxidants are normal and vital for processes such as cellular respiration and immunity, an imbalance could lead to cell and tissue death, DNA damage, and protein and fat degradation.

U.S.20110112352 discloses an apparatus and method for electromagnetic treatment, in which electromagnetic treatment devices are provided for treatment of tissue. These are intended to apply energy within a specific bandpass of frequencies of a target biological pathway, such as the binding of Calcium to Calmodulin, and thereby regulate the pathway. The device provides for example, a field having an amplitude of between about 1 µV/cm to about 100 mV/cm at the target tissue and a peak induced magnetic field between about 1 µT and about 20 µT. The control circuit generates a burst of waveforms having a burst duration of greater than 0.5 msec and a burst period of between about 0.1 to about 10 seconds to produce a signal that is above background electrical activity.

The use of most low frequency EMF has been in conjunction with applications of bone repair and healing. As such, EMF waveforms and current orthopedic clinical use of EMF waveforms comprise relatively low frequency components and are of low power, inducing maximum electrical fields in a millivolts per centimeter (mV/cm) range at frequencies under five KHz. A linear physicochemical approach employing an electrochemical model of cell membranes to predict a range of EMF waveform patterns for which bioeffects might be expected is based upon an assumption that cell membranes, and specifically ion binding at structures in or on cell membranes, are a likely EMF target.

Time-varying electromagnetic fields, comprising rectangular waveforms such as pulsing electromagnetic fields, and sinusoidal waveforms such as pulsed radio frequency fields ranging from several Hertz to an about 15 to an about 40 MHz range, may be clinically beneficial when used as an adjunctive therapy for a variety of musculoskeletal injuries and conditions.

U.S. Pat. No. 9,278,231 discloses a system for inducing cellular regeneration and/or degeneration processes and methods of treatment based on such processes through generating and applying a sequentially programmed magnetic field (SPMF) to the area to be treated. In the case of regeneration and degeneration of cells, the pulsing frequencies are in the range of about 0.1 to about 2000 Hz based on the indication of the disease type. A magnetic field generating device is provided comprising: a magnetically conductive hollow cylindrical base body; a funnel at one end of said magnetically conductive hollow cylindrical base body which increases in diameter as it extends from the cylindrical base body to a terminal rim-like portion; a magnetically conductive rod-like structure extending along a central axis through said hollow cylindrical base body into an interior of said funnel; and an electrical coil wound circumferentially around the magnetic field generating device from the other end of the hollow cylindrical base body to the rim-like portion of the funnel.

U.S. Pat. No. 9,278,231 notes that electromagnetic fields of certain frequency ranges and intensities are indigenous to living tissues and it has been found that inciting the inherent resonance by exogenous treatment using electromagnetic fields [EMF], electric fields, and magnetic fields can induce cellular regeneration and degeneration processes. EMF in a range from 0.1-150 Hz have been reported to stimulate bone cells. It has also been reported that bone resorption that normally parallels disuse can be prevented or even reversed by the exogenous induction of electric fields. Electromagnetic fields below 10 µV/cm, when induced at frequencies between 50 and 150 Hz for 1 h/day, are sufficient to maintain bone mass even in the absence of function. Reducing the frequency to 15 Hz makes the field extremely osteogenic. This frequency-specific sinusoidal field initiated more new bone formation than a more complex pulsed electromagnetic field (PEMF), though inducing only 0.1% of the electrical energy of the PEMF.

U.S. Pat. No. 8,968,172 discloses a cell excitation terminal and a therapeutic system using customized electromagnetic (EM) waves varying dynamically with time for excitation include one or more EM wave generators, each of the EM wave generators is connected to a central processing unit (CPU), and the CPU controls, according to a signal detected by a human body status detection device, the EM wave generator to send EM waves corresponding to a detected subject. The therapeutic system can perform remote management. A remote server optimizes and updates therapeutic waveforms of a patient constantly according to a therapeutic effect of the patient, thereby improving the therapeutic effect constantly.

U.S. Pat. No. 8,911,342 relates to an apparatus and a method for stimulating brain tissue with pulsed electromagnetic fields weaker than the limit for elicitation of the action potentials of the cells of the tissue to be stimulated, the apparatus comprising: at least one electrically conducting coil positioned at a bitemporal position such that hippocampus is stimulated by at least one magnetic field upon supplying a pulse to said coil as well as a coil positioned at a occipital and parietal position; and a pulse generation means operationally connected to said at least one coil for supplying a series of current pulses for conduction, allowing generation of pulsed electromagnetic fields sufficiently strong to cause protein activation, and weaker than the limit for elicitation of the action potentials of the cells of the tissue to be stimulated.

U.S. Pat. No. 9,427,598 relates to methods of treating neurological injury and conditions, in particular, traumatic brain injury and physiological responses arising from injury or conditions. These treatment methods can include the steps of generating a pulsed electromagnetic field from a pulsed electromagnetic field source and applying the pulsed electromagnetic field 1 in proximity to a target region affected by the neurological injury or condition to reduce a physiological response to the neurological injury or condition.

U.S. Pat. No. 9,421,357 discloses systems, apparatuses, and methods for providing non-transcranial electrical stimuli to a biological subject may employ a support structure, at least one waveform generator, and at least a first electrode and a second electrode. The system can be sized and dimensioned to be worn on a head of the biological subject and operable to deliver non-transcranial electrical stimuli to at least one of the temporomandibular joints of the biological subject.

The use of electrical energy to produce modifications in living tissue is well known. Electro-magnetic devices have been used to promote healing of broken bones. Barker (1981). Additionally, use of pulsed electro-magnetic fields (PEMF) to promote healing of bone tissue is described in U.S. Pat. No. 4,315,503 to Ryaby, et al. and in U.S. Pat. No. 3,890,953 to Kraus, et al. Use of electro-magnetic energy to arrest arthritic pain has been disclosed in U.S. Pat. No. 3,902,502 to Liss, et al. There is little agreement so far amongst researchers in the field as to the most effective pulse wave form, frequency, and voltage level for treatment of tissue disorders.

Wound repair involves cellular events such as cell migration, replication, synthesis and deposition of new connective tissue, remodeling and epidermal cell migration over dermal repair tissue. Many studies suggest that these events may be influenced by endogenous and exogenous electric or magnetic fields in both soft and hard tissue. Electrical stimulation using direct electrical currents or induced voltages and currents has been shown to affect wound healing. Typical methods for the use of electric current in the promotion of healing are those methods employing low intensity direct current (LIDC) and, more recently, pulsed electromagnetic fields (PEMF). Electric current was initially employed to promote the healing bone fractures, especially those fractures demonstrating non-union. Several patents have issued for methods and devices for the use of PEMF's to promote bone healing. U.S. Pat. No. 3,915,151 issued to Kraus describes a magnetic coil device for the induction of electric current by the application of a magnetic field to injured bones and related soft tissues. U.S. Pat. No. 4,233,965 issued to Fairbanks describes a similar method and device using PEMF's to induce an electric current for the healing of bone and connective tissue, improved to achieve a deeper penetration of electrical current, especially for the treatment of arthritis. U.S. Pat. No. 4,556,051, issued to Maurer describes a device and method for promoting the healing of fractured bones and related connective tissue through the simultaneous application of PEMF's and pulsed electric current in a fixed phase relationship to produce a net current in the region of the fractured bone generally perpendicular to the plane of the fracture. U.S. Pat. No. 4,674,482 issued to Waltonen, et al describes a method and device for the promotion of vasoconstriction through the application of PEMF's. The inventor describes the device as an "electric icepack." A biasing circuit is described that prevents the occurrence of a reverse polarity pulse upon the fall of the magnetic flux induced by the fall of the generated pulse, thereby diminishing high frequency ringing at the beginning of a treatment signal and improving the promotion of vasoconstriction. U.S. Pat. No. 4,461,300 issued to Christiensen describes a method and device employing cathodic LIDC to promote the healing of fractures and injuries to bones and related soft tissues. A specifically designed cathodic electrode implant assembly with a particular method of implantation at the fracture or bone defect site is disclosed.

U.S. Pat. No. 3,893,462 issued to Manning, which describes a method and device employing an undulating electrical signal having a wave form whose rise time differs from its fall time, in turn producing a voltage at the tissue level that is bipolar with the amplitude and frequency components of one polarity differing from those of the opposite polarity, effecting the bioelectrical signals at the cellular or tissue level, thereby artificially stimulating the healing of the cells and/or tissue.

With respect to PEMF's, Bassett (1984), discloses that when a dynamic, magnetic field passes through a static conductor, such as wound tissue, an electric field is induced in the conductor, with voltages of 1.0 to 1.5 millivolts per centimeter. Bassett states that the current induced varies with time. Bassett (1984) suggests that PEMF's promote collagen growth. Goodman (1983), describes the stimulation of messenger RNA specific activity by PEMF's of 0.1 G per micro second. Murray (1985) describes the increase in collagen production in cell cultures produced by low frequency PEMF's. The field was generated by a generator-driven pair of Helmholtz-aiding air cored coils. Leaper (1985), on the other hand, disclosed that a 400 Gauss magnetic field was found not to promote wound healing. McLeod (1987), describes the use of AC electric fields of 0.1-1000 Hz frequency to promote proline incorporation into fibroblast populated collagen matrices.

Pawluk (2015) provides a review of PEMF for pain, and notes that static EMFs have been used for centuries to control pain and other biologic problems. After thousands of patient-years of use globally, very little risk has been found to be associated with MF therapies (Markov, 2004). Standards and guidelines for safety have been promulgated and published (ICNIRP, 2010). The primary precautions or contraindications relate to implanted electrical devices, pregnancy (because of lack of data), and seizures with certain kinds of frequency patterns in seizure-prone individuals. MFs affect pain perception in many different ways. These actions are both direct and indirect. Direct effects of MFs are on neuron firing, calcium ion movement, membrane potentials, endorphin levels, nitric oxide, dopamine levels, acupuncture actions, and nerve regeneration. Indirect benefits of MFs from physiologic function enhancement are on circulation, muscle, edema, tissue oxygen, inflammation, healing, prostaglandins, cellular metabolism, and cell energy levels (Jerabek and Pawluk, 1996). Pain relief mechanisms vary by the type of stimulus used (Takeshige and Sato, 1996). For example, needling to the pain-producing muscle, application of a static MF or external qigong, or needling to an acupuncture point all reduce pain by different mechanisms. In guinea pigs, pain could be induced by reduction of circulation in the muscle (ischemia) and reduced by recovery of circulation. Muscle pain relief is induced by recovery of circulation due to the enhanced release of acetylcholine as a result of activation of the cholinergic vasodilator nerve endings innervated to the muscle artery (Takeshige and Sato, 1996).

Several authors have reviewed the experience with PEMFs in Eastern Europe (Jerabek and Pawluk, 1996) and elsewhere (Trock, 2000) and provided a synthesis of the typical physiologic findings of practical use to clinicians, resulting from magnetic therapies. These include, at a minimum, reduction in edema and muscle spasm/contraction, improved circulation, enhanced tissue repair, and natural antinociception. These are the fundamentals of the repair of cell injury. PEMFs have been used extensively in many conditions and medical disciplines, being most effective in treating rheumatic or musculoskeletal disorders. PEMFs produced significant reduction of pain, improvement of spinal functions, and reduction of paravertebral spasms. In clinical practice, PEMFs have been found to be an aid in the therapy of orthopedic and trauma problems (Borg et al., 1996). The ability of PEMFs to affect pain is at least in part dependent on the ability of PEMFs to positively affect human physiologic or anatomic systems. The human nervous system is strongly affected by therapeutic PEMFs (Prato et al., 2001). Animals exposed to static and extremely lowfrequency (ELF) MFs are also affected by the presence of light, which strengthens the effects of PEMFs (Prato et al., 1999). One of the most reproducible results of weak ELF MF exposure is an effect upon neurologic pain signal processing (Thomas and Prato, 2002). This evidence suggests that PEMFs would also be an effective complement for treating patients suffering from both chronic and acute pain.

The placebo response may explain as much as 40% of an analgesia response from any pain treatment (Colloca et al., 2013), and needs to be accounted for in research design to assure adequate sample sizes. However, aside from this aspect of accounting for the placebo effect, the central nervous system mechanisms responsible for the placebo response, that is, central cognitive and behavioral processes, can be addressed directly in managing pain and include medications, hypnosis, mindfulness meditation, and psychotherapy. In addition, these placebo response-related central processes appear to be an appropriate target with magnetic therapies for managing pain. Amplifying MF manipulation of cognitive and behavioral processes has been evaluated in animal behavior studies and in humans, affecting at the very least opiate receptors (Del Seppia et al., 2007). Therefore, amplifying the placebo response with centrally focused MFs would generally be expected to be additive to pain management using MF therapies elsewhere on the body.

Cell injury itself involves multiple processes (Kumar, 2007), which, if mitigated, can be expected to reduce the perception of pain and limit the results of the cell injury. Therefore, this is the goal of clinical management. If the cause of pain cannot be reduced or eliminated, then the goals of pain management shift to reducing the perception of pain or blocking the pain signal traffic otherwise. Research on the use of PEMFs for pain management focuses on the multiple mechanisms of the production of pain. The primary mechanisms of the production of pain in local tissue in response to cell injury include, to varying degrees, edema, apoptosis or necrosis, diminished vascular supply, reduced cellular energy production, and impaired repair processes. PEMF therapies address many of these different aspects of cell injury (Jerabek and Pawluk, 1996). Magnetic therapy increases the threshold of pain sensitivity (Thomas and Prato, 2002) and activates the anticoagulation system (Khamaganova et al., 1993), which increases circulation to tissue. PEMF treatment stimulates production of opioid peptides, activates mast cells and increases electric capacity of muscular fibers, helps with edema and pain before or after a surgical operation (Pilla, 2013), increases amino acid uptake (De Loecker et al., 1990), and induces changes in transmembrane energy transport enzymes, allowing energy coupling and increased biologic chemical transport work.

Healthy humans normally have reduced pain perception and decreased pain-related brain signals (Prato et al., 2001). Biochemical changes in the blood of treated patients are found that support the pain reduction benefit. PEMFs cause a significant improvement in normal standing balance in adult humans (Thomas et al., 2001). PEMFs couple with muscular processing or upper-body nervous tissue functions, which indicate CNS sensitivity that likely improves central pain processing.

Various kinds of PEMFs have been found to reduce pain. For example, various MFs applied to the head or to an extremity, for 1-60 min, with intervals between exposures from several minutes to several hours, randomly sequenced with sham exposures allowed the study of brain reactions by various objective measures (Kholodov, 1998). EEGs showed increased low-frequency rhythms. Low-frequency EEG rhythms may explain the common perception of relaxation and sleepiness with ELF EMFs. Even weak AC MFs affect pain perception and pain-related EEG changes in humans (Sartucci et al., 1997). A 2 h exposure to 0.02-0.07 mT ELF MFs caused a significant positive change in pain-related EEG patterns.

The benefits of PEMF use may last considerably longer than the time of use. This is a common clinical observation. In rats, a single exposure produces pain reduction both immediately after treatment and even at 24 h after treatment (Cieslar et al., 1994). The analgesic effect is still observed at the 7th and 14th day of repeated treatment and even up to 14 days after the last treatment. Repeated presentation of painful stimuli in rats can significantly elevate the threshold of response to painful stimuli. One group (Fleming et al., 1994) investigated the ability of magnetic pulse stimuli to produce increases in pain thresholds, simulating thalamic pain syndrome. Exposure to the PEMFs increased the pain threshold progressively over 3 days. Pain suppression was maintained on the second and third days relative to other treatments. The pain threshold following the third MF exposure was significantly greater than those associated with morphine and other treatments. Brain-injured and normal rats both showed a 63% increase in mean pain threshold. The mechanism may involve endorphins, having important implications for clinical practice and the potential for a reduction in reliance on habit-forming medications.

PEMFs promote healing of soft tissue injuries by reducing edema and increasing resorption of hematomas (Markov and Pilla, 1995), thereby reducing pain. Low-frequency PEMFs reduce edema primarily during treatment sessions. PEMFs at very high frequencies applied for 20-30 min cause decreases in edema lasting several hours following an exposure session. PEMF signals induce maximum electric fields in the mV/cm range at frequencies below 5 kHz.

Chronic pain often occurs from aberrant small neural networks with self-perpetuated neurogenic inflammation. It is thought that high-intensity pulsed magnetic stimulation (HIPMS) noninvasively depolarizes neurons and can facilitate recovery following injury (Ellis, 1993). HIPMS, intensity up to 1.17 T, was used to study recovery after injury in patients with posttraumatic/postoperative low-back pain, reflex sympathetic dystrophy (RSD), neuropathy, thoracic outlet syndrome, and endometriosis. The outcome VAS difference was 0.4-5.2 with sham treatments versus 0-0.5 for active treatments. The author proposed that the pain reduction was likely due to induced eddy currents.

Effects on the tissues of the body and the symptoms of pain have been found across a wide spectrum of electromagnetic frequencies, including high-frequency PEMFs. For example, significant reductions in pain were found in individuals with acute whiplash injuries using 27.12 MHz PEMF stimulation (Foley-Nolan et al., 1992). The same group (Foley-Nolan et al., 1990) had previously found that individuals with persistent neck pain lasting greater than 8 weeks had statistically significantly greater improvement in their pain compared to controls. The controls were then crossed over onto PEMF treatment and had similar results.

For more detailed discussion of the potential mechanisms of action of MFs to treat pain, see Markov (2004). The author discusses some of the parameters that may be necessary to properly choose a therapeutic MF with respect to the target tissue to be stimulated. The research literature on magnetic therapies for pain management is very variable in describing the particular parameters of the magnetic therapy apparatus being studied. This leaves the clinician at a significant disadvantage in determining which MFs produce the best results for the given condition being treated. Further, the author states, "during the past 25 years more than 2 million patients have been treated worldwide for a large variety of injuries, pathologies and diseases. This large number of patients exhibited a success rate of approximately 80%, with virtually no reported complications." The author goes on to describe a number of mechanisms of cellular action of EMFs that may be deemed responsible for the therapeutic benefit in improving pain. In another study, Shupak et al. (2004) looked at possible mechanisms or influencing factors for the effects of PEMFs on pain, especially on sensory and pain perception thresholds. It appears that MF exposure does not affect temperature perception but can increase pain thresholds, indicating an analgesic effect. Based on the review by Del Seppia et al. (2007), it appears that at least one of the mechanisms involved in PEMF effects on pain and nociception is the opiate receptor. Another study in rats (Fleming et al., 1994) found that there was an analgesic effect comparable to more noxious tactile stimulation, that is, stress-induced analgesia. There was an approximately 50% increase in the pain threshold in response to electrical current stimulation.

In a study to gain a better understanding of pain perception (Robertson et al., 2010), a functional magnetic resonance imaging study was done to assess how the neuromodulation effect of MFs influences the processing of acute thermal pain in normal volunteers. ELF MFs (from DC to 300 Hz) have been shown to affect pain sensitivity in snails, rodents, and humans. Because of this research, it is unlikely that a pure placebo response is involved. This neuroimaging study found changes in specific areas of the brain with pain stimuli that are definitely modified by low-intensity PEMF exposure.

Chronic pain is often accompanied with or results from decreased circulation or perfusion to the affected tissues, for example, cardiac angina or intermittent claudication. PEMFs have been shown to improve circulation (Guseo, 1992). Pain syndromes due to muscle tension and neuralgias improve.

Peripheral neuropathy can be an extremely painful condition that is very challenging to manage. Two randomized controlled studies failed to show significant results in diabetic peripheral neuropathy (DPN) (Wróbel et al., 2008; Weintraub et al., 2009). Another two studies showed significant improvements in DPN (Cieslar et al., 1995; Graak et al., 2009). There were significant methodological differences among the studies.

A large study (Weintraub et al., 2009) was conducted to determine whether repetitive and cumulative exposure to low-frequency PEMF to the feet can reduce neuropathic pain (NP) and influence nerve regeneration. Two-hundred and twenty-five patients with DPN stage II or III were randomized in a double-blind, placebo-controlled parallel study, across 16 academic and clinical sites in 13 states to PEMF or sham (placebo) devices. They applied their treatments 2 h per day to their feet for 3 months. Pain reduction scores were measured using a VAS, the neuropathy pain scale (NPS), and the patient's global impression of change (PGIC). A subset of subjects underwent serial 3 mm punch skin biopsies from three standard lower-limb sites for epidermal nerve fiber density (ENFD) quantification. There was a significant dropout rate of 13.8%. The PEMF versus sham group had reductions in DPN symptoms on the PGIC (44% versus 31%; p=0.04). There were no significant differences in the NP intensity on NPS or VAS. Of the 27 patients who completed serial biopsies, 29% of the PEMF group had an increase in the distal leg ENFD of at least 0.5 SDs, while none did in the sham group (p=0.04). Those with increases in distal thigh ENFD had significant decreases in pain scores. The conclusion was that PEMF at this dose was not effective specifically in reducing NP. However, neurobiological effects on ENFD, PGIC, and reduced itching scores were hopeful and suggest that future studies should be attempted with higher PEMF intensities 3000-5000 G, longer duration of exposure, and a larger biopsy cohort. Since most of the therapeutic approaches to DPN have poor success rates, relying mostly on the suppression of pain with medications, this study is encouraging in actually demonstrating potential nerve regeneration improvements.

Another randomized, placebo-controlled, double-blind study (Wróbel et al., 2008) was conducted to assess an ELF PEMF effect on pain intensity, quality of life and sleep, and glycemic control in patients with painful diabetic polyneuropathy. Sixty-one patients were randomized into a study group of 32 patients exposed to a low-frequency, low-intensity MF or a sham control group of 29 patients. Pain durations were greater than 2 years in both groups. Treatments were for 3 weeks, 20 min a day, 5 days a week. Questionnaires, completed at the beginning, after 1-3 and 5 weeks, included SFMPQVAS (pain evaluation), EuroQol EQ-5D, and MOS Sleep Scale. Significant reductions in pain intensity were seen in both the study group, VAS 73 mm at baseline versus 33 mm after 3 weeks, and controls, VAS 69 mm at baseline versus 41 mm after 3 weeks. The extent of pain reduction did not differ significantly between the groups at any time. The conclusion was that this low-intensity ELF PEMF, used for only 3 weeks, had no advantage over sham exposure in reducing pain intensity. In the Weintraub study, patients were treated for 3 months, providing a longer opportunity to produce sustainable changes in the tissues. Since neuropathy is a very stubborn problem to treat, it is likely that both of these neuropathy studies were too short for the severity of neuropathy present, treatment protocols, measures, and equipment used.

In another study (Graak et al., 2009) on NP, using low-power, low-frequency PEMF of 600 and 800 Hz, 30 patients, 40-68 years of age with DPN stages N1a, N1b, N2a, were randomly allocated to three groups of 10 in each. Groups 1 and 2 were treated with low-power 600 and 800 Hz PEMF, respectively, for 30 min for 12 consecutive days. Group 3 served as control on usual medical treatment. Pain and motor nerve conduction parameters (distal latency, amplitude, nerve conduction velocity) were assessed before and after treatment. They found significant reduction in pain and statistically significant ($p<0.05$) improvement in distal latency and nerve conduction velocity in experimental Groups 1 and 2. Using this particular protocol, low-frequency PEMF was seen to reduce NP as well as for retarding the progression of neuropathy even when applied for only a short span of time. What could happen with longer-term treatment remains to be determined.

Thirty-one patients with diabetes mellitus (type I and II), with intense symptoms of neuropathy, were treated (Cieslar et al., 1995). They had 20 exposures to variable sinusoidal PEMF, 40 Hz, 15 mT, every day for 12 min. Reduction of pain and paresthesias, vibration sensation, and improved muscle strength was seen in 85% of patients, all significantly better than sham controls.

Carpal tunnel syndrome is another form of neuropathy, affecting the median nerve at the wrist. There are many different approaches to the treatment of carpal tunnel syndrome, including surgery, with varying success. In a randomized, double-blinded, placebo-controlled trial (Weintraub and Cole, 2008), a commonly commercially available combination of simultaneous static and dynamic, rotating time-varying dynamic MFS was used to treat the wrist. There was a significant reduction of deep pain. Ten months of active PEMF resulted in improvement in nerve conduction and subjective improvement on examination (40%), pain scores (50%), and a global symptom scale (70%).

The neuropathy of postherpetic neuralgia, a very common and painful condition, often medically resistant, responded to PEMF (Kusaka et al., 1995). A combination static and pulsed MF device was placed on the pain/paresthesia areas or over the spinal column or limbs. Treatments continued until symptoms improved or adverse side effects occurred. Therapy was effective in 80%. This treatment approach shows that treatment for pain problems may either be localized to the area of pain or over the spinal column or limbs, away from the pain. Treatment over the appropriate related spinal segment offers the opportunity to interrupt the afferent pain signal traffic to the brain. This approach has been frequently used with success in Eastern European studies (Jerabek and Pawluk, 1996). Another author reported a more general clinical series in postherpetic pain in which better results happened in patients simultaneously suffering from neck and low-back pain (Di Massa et al., 1989).

Posttraumatic, late-stage RSD, or now called regional complex pain syndrome (CRPS), a form of neuropathy, is very painful and largely untreatable by standard medical approaches. In one report, ten 30 min PEMF sessions of 50 Hz followed by a further 10 sessions at 100 Hz plus physiotherapy and medication reduced edema and pain at 10 days (Saveriano and Ricci, 1989). There was no further improvement at 20 days. The author had a personal case treated with a 27.12 MHz PEMF signal, in a nurse who was almost completely disabled in her left upper extremity. She used her device for about an hour a day. Within about 1 month, she had about 70% recovery, and within 2 months, she had essentially normal function with no further sensitivity to touch, changes in temperature, etc. She maintained her recovery with continued treatments in the home setting.

Musculoskeletal conditions, especially with related pain, are most frequently treated with MF therapies. Among these, one of the most common conditions is lumbar arthritis, as a cause of back pain. Chronic low-back pain affects approximately 15% of the US population during their lifetime (Preszler, 2000). Given the current treatment options available through conventional medical therapy, with their attendant risks, there is a large unmet need for safe and effective alternative therapies (Institute of Medicine, 2005).

PEMFs of 35-40 mT give relief or elimination of pain about 90%-95% of the time for lumbar OA, improve results from other rehabilitation therapies, and secondarily, additionally improve related neurologic symptoms (Mitbreit et al., 1986). Even PEMFs of 0.5-1.5 mT used at the site of pain and related trigger points also help (Rauscher and Van Bise, 2001). Some patients remained pain free 6 months after treatment.

In a series of 240 patients treated in an orthopedic practice with PEMFs, patients had decreased pain (Schroter, 1976) from rheumatic illnesses, delayed healing process in bones, and pseudoarthritis, including those with infections, fractures, aseptic necrosis, venous and arterial circulation, RSD (all stages), osteochondritis dissecans, osteomyelitis, and sprains and strains and bruises. The clinically determined success rate approached 80%. About 60% of loosened hip prostheses have subjective relief of pain and walk better, without a cane. Even so, x-ray evidence of improvement was seen periodically, as evidenced by cartilage/bone reformation, including the joint margin. If the goal in pain management is to heal the underlying tissue, not just manage symptoms, evidence, typically from imaging studies, can drive the duration of treatment to obtain the most long-lasting and more permanent results.

The use of PEMFs is rapidly increasing and extending to soft tissue from its first applications to hard tissue (Pilla, 2013). EMF in current orthopedic clinical practice is frequently used to treat delayed and nonunion fractures, rotator cuff tendinitis, spinal fusions, and avascular necrosis, all of which can be very painful. Clinically relevant response to the PEMF is generally not always immediate, requiring daily treatment for upward of a year in the case of nonunion fractures. PRF applications appear to be best for the reduction of pain and edema. The acute tissue inflammation that accompanies the majority of traumatic and chronic injuries is essential to the healing process; however, the body often over-responds in the chronic lesion situation, and the resulting edema causes delayed healing and chronic pain. Edema reduction is an important target for PRF and PEMF applications.

Even chronic musculoskeletal pain treated with MFs for only 3 days, once per day, can eliminate and/or maintain chronic musculoskeletal pain (Stewart and Stewart, 1989). Small, battery-operated PEMF devices with very weak field strengths have been found to benefit musculoskeletal disorders (Fischer, 2002). Because of the low strength used, treatment at the site of pain may need to last between 11 and 132 days, between two times per week, 4 h each, and, if needed, continuous use. Use at night could be near the head, for example, beneath the pillow, to facilitate sleep. Pain scale scores are significantly better in the majority of cases. Conditions that can be considered for treatment are arthritis, lupus erythematosus, chronic neck pain, epicondylitis, patellofemoral degeneration, fracture of the lower leg, and RSD/CRPS.

Back pain or whiplash syndrome treated with a very low-intensity (up to 30 µT) PEMF twice a day for 2 weeks along with usual pain medications relieves pain in 8 days in the PEMF group versus 12 days in the controls (Thuile and Walzl, 2002). Headache is halved in the PEMF group, and neck and shoulder/arm pain improved by one-third versus medications alone. PEMFs have been found (Kjellman et al., 1999) to have more benefit in the treatment of neck pain in some research, compared to physical therapy, for both pain and mobility.

A blinded randomized study was conducted to compare European spa therapy (ST) with PEMF therapy in chronic neck pain (Forestier et al., 2007a). There was significantly greater improvement in the PEMF group than the ST group (p=0.02). As part of the earlier study, the authors also did a cost-benefit analysis (Forestier et al., 2007b).

One group evaluated pain and swelling after distal radius fractures after an immobilization period of 6 weeks (Cheing et al., 2005). Eighty-three patients were randomly allocated to receive 30 min of either ice plus PEMF (group A), ice plus sham PEMF (group B), PEMF alone (group C), or sham PEMF for 5 consecutive days (group D). All had a standard home exercise program. Outcome measures included a VAS for recording pain, volume displacement for measuring the swelling of the forearm, and a handheld goniometer for measuring the range of wrist motions. They were assessed, before treatment, and on days 1, 3, and 5 during treatment. At day 5, a significantly greater cumulative reduction in VAS as well as improved ulnar deviation ROM was found in group A than the other three groups. For volumetric measurement and pronation, participants in group A performed better than subjects in group D but not those in group B. The end result was that the addition of PEMF to ice therapy produces better overall treatment outcomes than ice alone, or PEMF alone, in pain reduction and ulnar ROM. This study points out the cumulative benefit of using both PEMFs and standard therapy, at least in radial fractures.

Many therapeutic approaches for treatment of lateral epicondylitis (tennis elbow) have been used, including local steroid injection and surgery. PEMFs have been found as a useful and safe candidate therapy. One group tested the efficacy of PEMF compared to sham PEMF and local steroid injection (Uzunca et al., 2007). Sixty patients with lateral epicondylitis were randomly and equally distributed into three groups as follows: group I received PEMF, group II sham PEMF, and group III a corticosteroid+anesthetic agent injection. Pain levels during rest, activity, nighttime, resisted wrist dorsiflexion, and forearm supination were investigated with VAS and algometer. All patients were evaluated before treatment, at the third week, and the third month. VAS values during activity and pain levels during resisted wrist dorsiflexion were significantly lower in group III than group I at the third week. Group I patients had lower pain during rest, activity, and nighttime than group III at the third month. PEMF appears to reduce lateral epicondylitis pain better than sham PEMF. Corticosteroid and anesthetic agent injections can be used in patients for rapid return to activities, along with PEMFs to produce a longer-standing benefit.

Another randomized sham-controlled study (Devereaux et al., 1985) on lateral humeral epicondylitis (tennis elbow) involved 30 patients with both clinical and thermographic evidence of tennis elbow. PEMF treatment, consisted of 15 Hz, delivering 13.5 mV and using a figure of eight coil with the loops over each epicondyle for 8 h a day in one or two sessions, for a minimum period of 8 weeks. They were significant improvements in grip strength at 6 weeks, with a slight decrease in difference at 8 weeks. There was little difference in the first 4 weeks. Since there were only 15 subjects in each treatment group, this study was probably underpowered for most of the other measurement indices used.

Osteoarthritis (OA) affects about 40 million people in the United States. OA of the knee is a leading cause of disability in the elderly. Medical management is often ineffective and creates additional side-effect risks. Many patients with OA of the knee/s undergo many soft tissue and intra-articular injections, physical therapy, and many, eventually, arthroscopies or joint replacements. An ELF sawtooth wave, 50 µT, whole-body and pillow applicator system has been in use for about 20 years in Europe. In one study using the system, applied 8 min twice a day for 6 weeks, it was shown to improve knee function and walking ability significantly (Pawluk et al., 2002). Pain, general condition, and well-being also improved. Medication use decreased. Plasma fibrinogen, C-reactive protein (a sign of inflammation), and the sedimentation rate all decreased by 14%, 35%, and 19% respectively. Sleep disturbances often contribute to increased pain perception. It was found to improve sleep, with 68% reporting good/very good results. Even after 1 year follow-up, 85% claim a continuing benefit in pain reduction. Medication consumption decreases from 39% at 8 weeks to 88% after 8 weeks.

In a randomized, placebo-controlled study (Ay and Evcik, 2009), PEMF of 50 Hz, 105 µT, applied for 30 min, was used in 55 patients with grade 3 OA for only 3 weeks for pain relief and enhancing functional capacity of patients with knee OA. Pain improved significantly in both groups relatively equally (p<0.000). However, there was significant improvement in morning stiffness and activities of daily living (ADL) compared to the control group. They did not find a beneficial symptomatic effect of PEMF in the treatment of knee OA in all patients.

In a rheumatology clinic study of knee OA (Pipitone and Scott, 2001), 75 patients received active PEMF treatment by a unipolar magnetic device or placebo for 6 weeks. The 9 V battery-operated device was <0.05 mT with a low-frequency coil of 2 kHz plus harmonics up to 50 kHz modulated on a 3, 7.8, or 20 Hz base frequency and an ultrahigh frequency coil with a 250 MHz modulated frequency plus harmonics of the same modulation as the LF coil. Patients were instructed to use the magnetic devices three times a day. The 7.8 Hz modulation frequency was prescribed for the morning and afternoon treatments, while the 3 Hz modulation frequency was prescribed for the evening. Baseline assessments showed that the treatment groups were equally matched.

Analysis at follow-up showed greater between group improvements in global scores of health status. Paired analysis showed significant improvements in the actively treated group in objective function, pain, disability, and quality of life at study end compared to baseline. These differences were not seen in the placebo-treated group.

In another randomized, double-blind, placebo-controlled clinical trial of knee OA in Denmark (Thamsborg et al., 2005), 83 patients had two 2 h of daily treatment, 5 days per week for 6 weeks. They were reevaluated at 2 and 6 weeks after treatment. Again, objective standardized measures were used. There was a significant improvement in ADL, stiffness, and pain in the PEMF-treated group. In the control group, there was no effect on ADL after 2 weeks and a weak change in ADL after 6 and 12 weeks. Even the control group had significant reductions in pain at all evaluations and in stiffness after 6 and 12 weeks. There were no between-group differences in pain over time. ADL score improvements for the PEMF-treated group appeared to be less with increasing age. When groups were compared, those <65 years of age had significant reduction in stiffness. While this tended to be a negative study, when looking at between-group comparisons, there were indications of improvement in ADLs and stiffness, especially in individuals younger than 65.

Twenty-seven OA patients treated with PEMF in a tube-like coil device for 18 half-hour exposures over 1 month had an average improvement of 23%-61% compared to 2%-18% in the placebo group (Trock et al., 1993). They were evaluated at baseline, midpoint of therapy, end of treatment, and 1 month later. The active treatment group had decreased pain and improved functional performance. Another study reported by the same group (Trock et al., 1994), including 86 patients with OA of the knee and cervical spine, showed significant changes from baseline for the treated patients at the end of treatment and at 1-month follow-up. Placebo patients also showed improvement but with less statistical significance at the end of treatment and had lost significance for most variables at 1-month follow-up. The study patients showed improvements in pain, pain on motion, patient overall assessment, and physician global assessment.

One study (Sutbeyaz et al., 2006) looked at the effect of PEMFs on pain, ROM, and functional status in patients with cervical osteoarthritis (COA). Thirty-four patients were included in a randomized double-blind study. PEMF was administrated to the whole body using a 1.8×0.6 m size whole body mat. They were on the mat for 30 min per session, twice a day for 3 weeks. Pain levels in the PEMF treatment group decreased significantly after therapy ($p<0.001$), with no change in the sham group. Active ROM, neck muscle spasm, and disability (NPDS) scores also improved significantly after PEMF therapy ($p<0.001$). No change was seen in the sham group. This study shows that PEMFs can give significant pain reduction in neck arthritis and can be used alone or with other therapies to give even greater benefits.

A 50 Hz pulsed sinusoidal MF, 35 mT field PEMF for 15 min, 15 treatment sessions, improves hip arthritis pain in 86% of patients. Average mobility without pain improved markedly (Rehacek et al., 1982). Forty-seven patients with periarthritis of the shoulder who were receiving outpatient physical therapy were randomized using a controlled triple-blind study design to conventional physical therapy or conventional physical therapy with pulsed MF therapy (Leclaire and Bourgouin, 1991). They received treatments three times a week for a maximum of 3 months. PEMF therapy was applied 30 min at a time at three different frequencies 10/15/30 Hz with matched intensities of 3/4/6 mT over the course of the therapy program. This study showed no statistically significant benefit from magnetotherapy in the pain score, ROM, or improvement of functional status in patients with periarthritis of the shoulder. There appeared to be a trend toward slightly worse baseline function of the magnetic therapy group. This would therefore suggest that treatment was not carried out for a sufficient time. An improvement in the design of the study would have been to follow the individuals until they had achieved either goal recovery or full recovery, as would happen in clinical practice. Another possibility for the lack of benefit for the pulsed magnetic therapy group is that the frequencies and intensities used are not optimized for this particular condition, given the length and the frequency of treatments per week.

Fibromyalgia (FM) is a complex syndrome, primarily affecting women. PEMFs can frequently be very helpful. In one study (Sutbeyaz et al., 2009), 56 women with FM, aged 18-60 years, were randomly assigned to either PEMF or sham therapy, 30 min per session, twice a day for 3 weeks. Treatment outcomes were assessed after treatment and at 4 weeks, showing significant improvements in test scores at the end of therapy and at 4-week follow-up. The sham group also showed improvement at this time on all outcome measures except the specific FM questionnaire. So, low-frequency PEMF therapy can improve at least some general FM symptoms. A low-intensity PEMF (400.tT) in a portable device fitted to their head was found to help FM. In a randomized, double-blind, sham-controlled clinical trial (Thomas et al., 2007), patients with either chronic generalized pain from FM (n=17) or chronic localized musculoskeletal or inflammatory pain (n=15) were exposed in treatments twice daily for 40 min over 7 days. A VAS scale was used. There was a positive difference with PEMF over sham treatment with FM, although not quite reaching statistical significance ($p=0.06$). The same level of benefit was not seen in those without FM. In patients with other causes of chronic, nonmalignant pain, either longer periods of exposure are necessary or other approaches need to be considered.

The effect of specific PEMF exposure on pain and anxiety ratings was investigated in two patient populations (Shupak et al., 2006). A double-blind, randomized, placebo-controlled parallel design was used on the effects of an acute 30 min MF exposure (less than or equal to 400 μT; less than 3 kHz) on VAS-assessed pain and anxiety ratings in female RA and FM patients who received either the PEMF or sham exposure treatment. A significant pre-post effect was present for the FM patients, $p<0.01$. There was no significant reduction in VAS anxiety ratings pre-to-post-exposure.

An in vivo study of PEMFs (Shafford H L, et al. 2002) was done in dogs postoperatively after ablation of ovaries and uterus to see how pain is affected and interacts with postoperative morphine analgesia. Sixteen healthy dogs were examined within 6 h postoperatiion at eight different time points. There were four groups: (1) control group (NaCl administration), (2) postoperative PEMF exposure (NaCl administration), (3) postoperative morphine application, and (4) postoperative morphine application plus PEMF exposure. The PEMF was 0.5 Hz, exposure intermittent, 20 min field on/20 min field off for 6 h, whole-body exposure. At 30 min, the total pain score for group 4 was significantly less than for the control group, but not significantly different from group 2 or 3. The results suggest that PEMF may augment morphine analgesia or be used separately postoperatively after invasive abdominal procedures.

After breast augmentation surgery, patients (Hedén and Pilla, 2008) applied a portable and disposable noninvasive, high-frequency and low-intensity PEMF device in a double-blind, randomized, placebo-controlled study. Healthy females undergoing breast augmentation for aesthetic reasons were separated into three cohorts: (n=14) receiving bilateral PEMF treatment, (n=14) receiving bilateral sham devices, and (n=14) an active device to one breast and a sham device to the other breast. Pain levels were measured twice daily through the seventh day after surgery (POD 7), and postoperative analgesic use was also tracked. VAS scores decreased in the active cohort by almost three times the sham cohort by POD 3 (p<0.001) and persisted at this level to POD 7. Postoperative pain medication use decreased nearly three times faster in the active versus the sham cohorts by POD 3 (p<0.001). These results can be extended to include the use of this form of PEMF for the control of almost any situation of postoperative pain, especially involving surgery on superficial physical structures.

In another surgical study, this time post breast reduction for symptomatic macromastia, PEMFs were studied, not only on their results on postoperative pain, but also on potential mechanisms, including changes to cytokines and angiogenic factors in the wound bed (Rodhe et al., 2010). Twenty-four patients were randomized in a double-blind, placebo-controlled, randomized fashion to a sham control or a low-intensity 27.12 Hz PEMF configured to modulate the calmodulin-dependent nitric oxide signaling pathway. Pain levels were measured by VAS, and narcotic use was recorded. The PEMF used produced a 57% decrease in mean pain scores at 1 h (p<0.01) and a 300% decrease at 5 h (p<0.001), persisting to 48 h postoperatively in the active versus the control group, along with a concomitant 2.2-fold reduction in narcotic use in active patients (p=0.002). Mean IL-1$\beta$ in wound exudates was 275% lower (p<0.001), suggesting fairly rapid reductions in acute posttraumatic inflammation.

On the other hand, some research has found a lack of benefit of PEMFs postoperatively. Pain after elective inguinal hernia repair was evaluated in a double-blind randomized, non-PEMF controlled trial using a high-frequency low-intensity portable PEMF device (Reed et al., 1987). The device had an output rate of 320 Hz, pulse width of 60 µs, and maximum power output of 1 W. Treatment was 15 min twice a day, over and under the thigh. VAS at 24 and 48 h postoperatively showed no difference between treated and untreated groups. This study most likely used treatment times that were too short for the intensities used, and the electrodes were placed remote to the actual wound, not over the surgical site.

Severe joint inflammation following trauma, arthroscopic surgery, or infection can damage articular cartilage; thus, every effort should be made to protect cartilage from the catabolic effects of proinflammatory cytokines and stimulate cartilage anabolic activities. A pilot, randomized, prospective, and double-blind study (Zorzi et al., 2007) was done to evaluate the effects of PEMFs (75 Hz, rectangular) after arthroscopic treatment of knee cartilage. Patients with knee pain were recruited and treated by arthroscopy with chondroabrasion and/or perforations and/or radio frequencies. There were two groups: lower-intensity control (MF at 0.05 mT) and active (MF of 1.5 mT). PEMFs were used for 90 days, 6 h per day. Objective measures were used before arthroscopy, and after 45 and 90 days, the use of anti-inflammatories (NSAIDs) was recorded. Three-year follow-up interviews were also used (n=31). Knee score values at 45 and 90 days were higher in the active group at 90 days (p<0.05). NSAID use was 26% in the active group and 75% in the control group (p=0.015). At 3-year follow-up, the percent completely recovered was higher in the active group (p<0.05).

Anterior cruciate ligament reconstruction, now a common surgical procedure, is usually performed by a minimally invasive arthroscopic approach. Even so, arthroscopy may elicit an inflammatory joint reaction detrimental to articular cartilage. PEMFs would be expected to mitigate some of these inflammation reactions. To study this possibility, a prospective, randomized, and double-blind study was done on 69 patients with a 75 Hz, 1.5 mT device, 4 h per day for 60 days versus sham device (Benazzo et al., 2008). At follow-up, active treatment patients showed a statistically significant faster recovery (p<0.05). The use of anti-inflammatories was less frequent (p<0.05). Joint swelling and return to normal ROM occurred faster (p<0.05). The 2-year follow-up did not show statistically significant difference between the two groups. In addition, a subset analysis of 29 patients (15 in the active group; 14 in the placebo group) who concurrently had meniscectomy, function scores between the two groups were even larger than observed in the whole study. So this particular PEMF signal is expected to shorten postoperative recovery time and limit joint inflammation.

Noninflammatory chronic pelvic pain syndrome (CPPS) can be quite disabling in both men and women, frequently with no adequate treatment options. A study (Leippold et al., 2005) was designed to prospectively evaluate sacral magnetic stimulation as a treatment option for patients with noninflammatory CPPS (CPPS, category IIIB). Fourteen men were treated with sacral magnetic stimulation, 10 treatment sessions once a week for 30 min at a frequency of 50 Hz. Twelve of fourteen men reported improvement but only during the time of stimulation. Inventory scores before and after treatment did not change. There was no sustained effect beyond the time of stimulation on the mean scores for pain, micturition complaints, or quality of life. Sacral magnetic stimulation in patients with CPPS IIIB reduces pain only during stimulation. The fact the pain relief is obtained during treatment is notable and valuable. Because this level of frequency of treatments is less likely to induce healing in the tissues causing the pain syndrome, it may be reasonable to expect only a reduction in pain during the treatment course and not a more enduring benefit. While this treatment approach does not appear to be useful, it remains to be seen whether a change in the protocol may produce more enduring results.

Gynecologic pelvic pain may also benefit from PEMFs. A high-voltage, high intensity, pulsed stimulation (1-30 pulses/second) system (Jorgensen et al., 1994) was used in the setting of ruptured ovarian cysts, postoperative pelvic hematomas, chronic urinary tract infection, uterine fibrosis, dyspareunia, endometriosis, and dysmenorrhea. Ninety percent of patients experienced marked rapid relief from pain, with pain subsiding within 1-3 days after PEMF treatment, eliminating supplementary analgesics.

In dentistry, periodontal disease may cause bone resorption severe enough to require bone grafting. Grafting is followed by moderate pain peaking several hours afterward. Repeated PEMF exposure for 2 weeks eliminates pain within a week. Even single PEMF exposure to the face for 30 min of a 5 mT field and related conservative treatment produce much lower pain scores versus controls (Tesic et al., 1999).

Results of PRF PEMF in a case series either eliminates or improves, even at 2 weeks following therapy, pain in 80% of patients with pelvic inflammatory disease, 89% with back pain, 40% with endometriosis, 80% with postoperative pain, and 83% with lower abdominal pain of unknown cause (Punnonen et al., 1980).

PEMFs have been found to be helpful in headaches. For migraine headaches, high-frequency (5361 gHz) PEMFs applied to specific acupuncture points on the inner thighs for at least 2 weeks are effective short-term therapy (Sherman et al., 1999). Longer exposures lead to greater reduction of headache activity. One month after a treatment course, 73% of patients report decreased headache activity versus 50% of placebo treatment. Another 2 weeks of treatment after the 1-month follow-up gives an additional 88% decrease in headache activity. Patients with headache treated with a PEMF for 15 days after failing acupuncture and medications get effective relief of migraine, tension, and cervical headaches at about 1 month after treatment (Prusinski et al., 1987). They have at least a 50% reduction in frequency or intensity of the headaches and reduction in analgesic drug use. Cluster and posttraumatic headaches do not respond as well.

PEMFs of various kinds, strengths, and frequencies included have been found to have good results in a wide array of painful conditions. There is little risk when compared to the potential invasiveness of other therapies and the risk of toxicity, addiction, and complications from medications. This creates an ideal setup for clinicians to attempt PEMFs before other more potentially harmful treatments are attempted, especially for long-term treatment of chronic pain conditions.

REFERENCES

Aktas I, Akgun K, Cakmak B. (August 2007) Therapeutic effect of pulsed electromagnetic field in conservative treatment of subacromial impingement syndrome. Clin Rheumatol 26(8): 1234-1239.

Aleman A. (August 2013) Use of repetitive transcranial magnetic stimulation for treatment in psychiatry. Clin Psychopharmacol Neurosci 11(2): 53-59.

Alvarez, O. M., Mertz, P. M. Smerbeck, R. V. and Eaglstein, W. H. The Healing of Superficial Skin Wounds is Stimulated by External Electrical Current. J. Invest. Dermatol. 81, 144-148 (1983).

Arnold M D, Thornbrough L M. (August 1999) Treatment of musculoskeletal pain with traditional Chinese herbal medicine. Phys Med Rehabil Clin N Am 10(3): 663-671, ix-x.

Assimacopoulos, D. Low Intensity Negative Electric Current in the Treatment of Ulcers of the Leg Due to Chronic Veinous Insufficiency. Am. J. Surg. 115, 683-687 (1968).

Assimacopoulos, D. Wound Healing Promotion by the Use of Negative Electric Current, Am. Surg. 34, 423-431 (1968).

Athenstaedt, H. Permanent Electric Polarization of the Meninges of Man, Z. Zellforsh 98, 300-322 (1969).

Ay S, Evcik D. (April 2009) The effects of pulsed electromagnetic fields in the treatment of knee osteoarthritis: A randomized, placebo-controlled trial. Rheumatol Int 29(6): 663-666.

Barker, A. T., The Design of a Clinical Electro-Magnetic Bone Stimulator, Clinical Physical Physiology Measurement, February, 1981, Volume II, No. 1, Pages 9-16.

Bassett C, Schink-Ascani M. Long-term pulsed electromagnetic field (PEMF) results in congenital pseudarthrosis. Calcified Tissue International. 1991; 49(3):216-20.

Bassett, C. A. L. Biophysical Principles Affecting Bone Structure, in: The Biochemistry and Physiology of Bone, Vol. II, Bourne, G. H., Ed., Adacemic Press, New York, 1971, 1.

Bassett, C. A. L. The Development and Application of Pulsed Electromagnetic Fields (PEMFs) for Ununited Fractures and Arthrodeses. Orthoped. Clinics of North Am. 15, 61-87 (1984).

Bassett, C. A. L., Mitchell, S. N. and Gaston, S. R. Treatment of Ununited Tibial Diaphyseal Fractures with Pulsing Electromagnetic Fields, J. Bone Jt. Surg. 63-A, 511-523 (1981).

Behrens B, Michlovitz S. Physical Agents Theory and Practice. Second ed. Philadelphia: F. A. Davis; 2006. p. 145

Benazzo F, Zanon G, Pederzini L et al. (June 2008) Effects of biophysical stimulation in patients undergoing arthroscopic reconstruction of anterior cruciate ligament: Prospective, randomized and double blind study. Knee Surg Sports Traumatol Arthrosc 16(6): 595-601.

Binder A, Parr G, Hazleman B, Fitton-Jackson S. Pulsed Electromagnetic Field Therapy Of Persistent Rotator Cuff Tendinitis: A Double-blind Controlled Assessment. The Lancet. 1984; 323(8379):695-8.

Borg M J, Marcuccio F, Poerio A M et al. (October 1996) Magnetic fields in physical therapy. Experience in orthopedics and traumatology rehabilitation. Minerva Med 87(10): 495-497.

Brighton, C. T., Adler, S., Black, J., Itada, N., Friedenberg, Z. B. Cathodic oxygen consumption and electrically induced osteogenesis. Clin. Orth. Rel. Res. 107, 277-282 (1975).

Brighton, C. T., Black, J., Friedenberg, Z. B., Esterhai, J. L. Day, L. J. and Connolly, J. F. A Multicenter Study of the Treatment of Non-union with Constant Direct Current, J. Bone Jt. Surg. 63-A, 2-13 (1981).

Carey, L. C. and Lepley, L. D. Effect of Continuous Direct Electric Current on Healing Wounds. Surg. Forum 13, 33-36 (1962).

Carley, P. J. and Wainapel, S. F. Electrotherapy for Acceleration of Wound Healing: Low Intensity Direct Current. Arch. Phys. Med. Rehab. 66, 443-446 (1985).

Caselli M A, Clark N, Lazarus S, Velez Z et al. (January 1997) Evaluation of magnetic foil and PPT insoles in the treatment of heel pain. J Am Podiatr Med Assoc 87(1): 11-16.

Chang W H-S, Chen L-T, Sun J-S, Lin F-H. Effect of pulse-burst electromagnetic field stimulation on osteoblast cell activities. Bioelectromagnetics. 2004; 25(6): 457-65.

Cheing G L, Wan J W, Kai Lo S. (November 2005) Ice and pulsed electromagnetic field to reduce pain and swelling after distal radius fractures. J Rehabil Med 37(6): 372-377.

Cheng, N., VanHoof, H., Brockx, E., Hoogmartens, M. J., Mulier, J. C., DeDijcker, F. J. Sansen, W. M. and DeLoecker, W. The effects of electric currents on ATP generation, protein synthesis and membrane transport in rat skin. Clin. Orth. Rel. Res. 171, 264-572 (1982).

Cieslar G, Mrowiec J, Sieron A et al. (1994) The reactivity to thermal pain stimulus in rats exposed to variable magnetic field. Balneol Pol 36(3-4): 24-28.

Cieslar G, Sieron A, Radelli J. (1995) The estimation of therapeutic effect of variable magnetic fields in patients with diabetic neuropathy including vibratory sensibility. Balneol Pol 37(1): 23-27.

Colbert A P, Cleaver J, Brown K A et al. (September 2008) Magnets applied to acupuncture points as therapy—A literature review. Acupunct Med 26(3): 160-170.

Colbert A P, Markov M S, Banerji M et al. (1999) Magnetic mattress pad use in patients with fibromyalgia: A randomized double-blind pilot study. J Back Musculoskelet Rehabil 13: 19-31.

Colloca L, Klinger R, Flor H et al. (April 2013) Placebo analgesia: Psychological and neurobiological mechanisms. Pain 154(4): 511-514.

Covall D J, Wasilewski S A. (1992) Roentgenographic changes after arthroscopic meniscectomy: Five-year follow-up in patients more than 45 years old. Arthroscopy 8(2): 242-246.

De Loecker W, Cheng N, Delport P H. Effects of pulsed electromagnetic fields on membrane transport. In Emerging Electromagnetic Medicine. Ed's: O'Connor M E, Bentall, R H C, Monahan, J C. New York: Springer-Verlag, 1990, pp. 45-59.

DeHaas, W. G., Watson, J. and Morrison, D. M. Non-Invasive Treatment of Ununited Fractures of the Tibia Using Electrical Stimulation. J. Bone. Jt. Surg. 62-B, 465-470 (1980).

Del Seppia C, Ghione S, Luschi P et al. (2007) Pain perception and electromagnetic fields. Neurosci Biobehav Rev 31(4): 619-642.

Delle Monache S, Alessandro R, Iorio R, Gualtieri G, Colonna R. Extremely low frequency electromagnetic fields (ELF-EMFs) induce in vitro angiogenesis process in human endothelial cells. Bioelectromagnetics. 2008; 29(8):640-8.

Devereaux M D, Hazleman B L, Thomas P P. (October-December 1985) Chronic lateral humeral epicondylitis—A double-blind controlled assessment of pulsed electromagnetic field therapy. Clin Exp Rheumatol 3(4): 333-336.

Di Massa A, Misuriello I, Olivieri M C et al. (1989) Pulsed magnetic fields. Observations in 353 patients suffer-ing from chronic pain. Minerva Anestesiol 55(7-8): 295-299.

Doillon, C. J. and Silver, F. H. Collagen Wound Dressing: Effect of Hyaluronic Acid and Fibronectin, Biomaterials 7, 3-8 (1986).

Doillon, C. J., Dunn, M. G., Berg, R. A. and Silver, F. H. Collagen Deposition During Wound Repair. Scanning Electron Microscopy, 11, 897-903 (1985).

Doillon, C. J., Whyne, C. F., and Berg, R. A. Fibroblast Growth on a Porous Collagen Sponge Containing Hyaluronic Acid and Fibronectin, Biomaterials 8, 195-200 (1987).

Doillon, C. J., Whyne, C. F., Berg, R. A., Olson, R. M. and Silver, F. H. Fibroblast-Collagen Sponge Interactions and the Spatial Deposition of Newly Formed Collagen Fibers In Vitro and In Vivo, Scanning Electron Microscopy III, 1313-1320 (1984).

Doillon, C. J., Whyne, C. F., Brandwein, S. and Silver, F. H. Collagen-Based Wound Dressings: Control of the Pore Structure and Morphology. J. Biomed. Mater. Res. 20, 1219-1228 (1986).

Ellis W V. (1993) Pain control using high-intensity pulsed magnetic stimulation. Bioelectromagnetics 14(6): 553-556.

Eriksen W, Sandvik L, Bruusgaard D. (October 1996) Does dietary supplementation of cod liver oil mitigate musculoskeletal pain? Eur J Clin Nutr 50(10): 689-693.

Farndale R, Murray J. Pulsed electromagnetic fields promote collagen production in bone marrow fibroblasts via athermal mechanisms. Calcified Tissue International. 1985; 37(2):178-82.

Fernandez M I, Watson P J, Rowbotham D J. (August 2007) Effect of pulsed magnetic field therapy on pain reported by human volunteers in a laboratory model of acute pain. Br J Anaesth 99(2): 266-269.

Fischer G. (2002) Relieving pain in diseases of the musculoskeletal system with small apparatuses that produce magnetic fields, Personal communication.

Fleming J L, Persinger M A, Koren S A. (1994) Magnetic pulses elevate nociceptive thresholds: Comparisons with opiate receptor compounds in normal and seizure-induced brain-damaged rats. Electro Magnetobiol. 13(1): 67-75.

Foley-Nolan D, Barry C, Coughlan R J et al. (1990) Pulsed high frequency (27 MHz) electromagnetic therapy for persistent neck pain. A double blind, placebo-controlled study of 20 patients. Orthopedics 13(4):445-451.

Foley-Nolan D, Moore K, Codd M et al. (1992) Low energy high frequency pulsed electromagnetic therapy for acute whiplash injuries. A double blind randomized controlled study. Scand J Rehabil Med 24(1): 51-59.

Forestier R, Françon A, Saint Arroman F et al. (April 2007b) Are SPA therapy and pulsed electromagnetic field therapy effective for chronic neck pain? Randomised clinical trial. Second part: Medicoeconomic approach. Ann Readapt Med Phys 50(3): 148-153.

Forestier R, Françon A, Saint-Arromand F et al. (April 2007a) Are SPA therapy and pulsed electromagnetic field therapy effective for chronic neck pain? Randomised clinical trial. First part: Clinical evaluation. Ann Readapt Med Phys 50(3): 140-147.

Frank, C. B., and Szeto, A. Y. J. A Review of Electromagnetically Enhanced Soft Tissue Healing. IEEE Engineering in Medicine and Biology Magazine 27-32 (December 1983).

Friedenberg, Z., Andrews, E. T. Smolenski, B. I. Pearl, B. W. and Brighton, C. T. Bone Reaction to Various Amounts of Direct Current. Surg. Gyn. Obstet. 131, 894-899 (1970).

Fukada, E. Piezoelastic Properties of Biological Macromolecules, Advances Biophys 6, 121-155 (1974).

Ganesan K, Gengadharan A C, Balachandran C, Manohar B M, Puvanakrishnan R. Low frequency pulsed electromagnetic field—a viable alternative therapy for arthritis. Indian J Exp Biol. 2009; 47(12):939-48.

Gault, W. R. and Gatens, P. F. Use of Low Intensity Direct Current in Management of Ischemic Skin Ulcers. Phys. Ther. 56, 265-269 (1976).

Gensler, W. Electrochemical Healing Similarities Between Animals and Plants. Biophys. J. 27, 461-466 (1979).

Gómez-Ochoa I, Gómez-Ochoa P, Gómez-Casal F, Cativiela E, Larrad-Mur L. Pulsed electromagnetic fields decrease proinflammatory cytokine secretion (IL-1β and TNF-α) on human fibroblast-like cell culture. Rheumatology International. 2011; 31(10):1283-9.

Goodman, R., Basset, C. A. L., and Henderson, A. S. Pulsing Electromagnetic Fields Induce Cellular Transcription. Science 220, 1283-1285 (1983).

Gordon G A. Designed electromagnetic pulsed therapy: Clinical applications. Journal of Cellular Physiology. 2007; 212(3):579-82.

Graak V, Chaudhary S, Bal B S et al. (April 2009) Evaluation of the efficacy of pulsed electromagnetic field in the management of patients with diabetic polyneuropathy. Int J Diabetes Dev Ctries 29(2): 56-61.

Grodzinsky, A. J. Electromechanical and Physiochemical Properties of Connective Tissue, CRC Critical Reviews in Biomedical Engineering 9, 133-199 (1983).

Guseo A. Physiological effects of pulsing electromagnetic field. In First Congress of European Bioelectromagnetics Association (EBEA), Brussels, Belgium, January 1992, s.31.

Haldeman S, Rubinstein S M. (January 1993) The precipitation or aggravation of musculoskeletal pain in patients receiving spinal manipulative therapy. J Manipulat Physiol Ther 16(1): 47-50.

Han T R, Shin H I, Kim I S. (July 2006) Magnetic stimulation of the quadriceps femoris muscle: Comparison of pain with electrical stimulation. Am J Phys Med Rehabil 85(7): 593-599.

Harlow T, Greaves C, White A, Brown L, Hart A, Ernst E. (2004) Randomised controlled trial of magnetic bracelets for relieving pain in osteoarthritis of the hip and knee. BMJ 329: 1450-1454.

Hedén P, Pilla A A. (July 2008) Effects of pulsed electromagnetic fields on postoperative pain: A double-blind randomized pilot study in breast augmentation patients. Aesthetic Plast Surg 32(4): 660-666.

Huang L Q, He H C, He C Q, Chen J, Yang L. Clinical update of pulsed electromagnetic fields on osteoporosis. Chin Med J. 2008; 121(20):2095-9.

ICNIRP (2010) Guidelines for limiting exposure to time-varying electric and magnetic fields (1 Hz-100 kHz). Health Phys 99(6): 818-836.

Institute of Medicine (TOM) of the National Academies. Complementary and Alternative Medicine in the United States. Washington, D.C.: The National Academies Press, 2005, p. 1.

Jerabek J, Pawluk W. Magnetic Therapy in Eastern Europe: A Review of 30 Years of Research. Chicago, Ill.: Advanced Magnetic Research of the Delaware Valley, 1996.

Jorgensen W A, Frome B M, Wallach C. (1994) Electrochemical therapy of pelvic pain: Effects of pulsed electromagnetic fields (PEMF) on tissue trauma. Eur J Surg 160(574 Suppl): 83-86.

Junquiera, L. C. U., Bignolas G. and Bretani, R. R. Picro-Sirius Staining Plus Polarization Microscopy, A Specific Method for Collagen Detection in Tissue Sections. Histochem. J. 11, 477-455 (1979).

Kennedy W F, Roberts C G, Zuege R C, Dicus W T. Use of pulsed electromagnetic fields in treatment of loosened cemented hip prostheses. A double-blind trial. Clin Orthop Relat Res. 1993; 286(286):198-205.

Khamaganova I V, Boinich Z V, Arutiunova E S. (1993) Clinical aspects of the use of a pulsed magnetic field. Fizicheskaia Meditzina 3(1-2): 35-37.

Kholodov Y A. A non-specific initial response of brain to various electromagnetic fields. In International Meeting of Electromagnetic Fields: Biological Effects and Hygienic Standards, Moscow, Russia, May 1998.

Kjellman G V, Skargren E I, Oberg B E. (1999) A critical analysis of randomised clinical trials on neck pain and treatment efficacy. A review of the literature. Scand J Rehabil Med 31(3): 139-152.

Komanowsky, M. Production of Comminuted Collagen for Novel Applications. J. Am. Leather Chem., 69, 410-411 (1974).

Konikoff, J. J. Electrical Promotion of Soft Tissue Repairs. Ann. Biomed. Engng. 4, 1-5 (1976).

Kumar V. Chapter 1: Cell injury, cell death and adaptations. In Robbins and Cotran Pathologic Basis of Disease, Professional Edition Philadelphia, Elsevier. 8th edn., 2007. Vinay Kumar, MBBS, MD, FRCPath, Abul K. Abbas, MBBS and Jon C. Aster, MD, PhD Kusaka C, Seto A, Nagata T et al. (1995) Pulse magnetic treatment and whole-body, alternating current magnetic treatment for post-herpetic neuralgia. J Jpn Biomagnet Bioelectromagnet Soc 8(2): 29-38.

Lavine, L. S., Lustrin, I., Shomos, M. H., Rinaldi, R. A. and Liboff, A. R. Electric Enhancement of Bone Healing, Science 175, 1118-1121 (1972).

Leaper, D. J., Foster, M. E., Brennan, S. S. and Davies, P. W. An Experimental Study of the Influence of Magnetic Fields on Soft-Tissue Wound Healing. J. of Trauma 25, 1083-1084 (1985).

Leclaire R, Bourgouin J. (April 1991) Electromagnetic treatment of shoulder periarthritis: A randomized controlled trial of the efficiency and tolerance of magnetotherapy. Arch Phys Med Rehabil 72(5): 284-287.

Lefaucheur J P, Drouot X, Menard-Lefaucheur I et al. (April 2004) Neurogenic pain relief by repetitive transcranial magnetic cortical stimulation depends on the origin and the site of pain. J Neurol Neurosurg Psychiatr 75(4): 612-616.

Leippold T, Strebel R T, Huwyler M et al. (2005) Sacral magnetic stimulation in noninflammatory chronic pelvic pain syndrome. BJU Int 95: 838-841.

Levy R, Deer T R, Henderson J. (March-April 2010) Intracranial neurostimulation for pain control: A review. Pain Phys 13(2): 157-165.

Lin M L, Lin M H, Fen J J et al. (2010) A comparison between pulsed radiofrequency and electro-acupuncture for relieving pain in patients with chronic low back pain. Acupunct Electrother Res 35(3-4): 133-146.

Marino, A. A. and Becker, R. O. The Effect of Electric Current on Rat Tail Tendon Collagen in Solution, Calc. Tiss. Res. 4, 330-338 (1970).

Markov M. Pulsed electromagnetic field therapy history, state of the art and future. The Environmentalist. 2007; 27(4):465-75.

Markov M S, Pilla A A. (1995) Electromagnetic field stimulation of soft tissue: Pulsed radiofrequency treatment of post-operative pain and edema. Wounds 7(4): 143-151.

Markov M S. Magnetic and electromagnetic field therapy: Basic principles of application for pain relief. In Bioelectromagnetic Medicine. Ed's: Rosch, P J and Markov, M S. New York, Marcel Dekker, 2004, pp. 251-264.

Mattei M D, Caruso A, Pezzetti F, Pellati A, Stabellini G, Sollazzo V, et al. Effects of Pulsed Electromagnetic Fields on Human Articular Chondrocyte Proliferation. Connective Tissue Research. 2001; 42(4):269-79.

McLeod, K. J., Lee, R. C. and Ehrlich, H. P. Frequency Dependence of Electric Field Modulation of Fibroblast Protein Synthesis, Science 236, 1465-1468 (1987).

Mitbreit I M, Savchenko A G, Volkova L P et al. (1986) Low-frequency magnetic field in the complex treatment of patients with lumbar osteochondrosis. Ortop Travmatol Protez—10: 24-27.

Murray, J. C. and Farndale, R. W. Modulation of Collagen Production in Cultured Fibroblasts by a Low-Frequency, Pulsed Magnetic Field. Biochem. Biophys. Acta 838, 98-105 (1985).

Nelson F R, Zvirbulis R, Pilla A A. (August 2013) Non-invasive electromagnetic field therapy produces rapid and substantial pain reduction in early knee osteoarthritis: A randomized double-blind pilot study. Rheumatol Int 33(8): 2169-2173.

Panagopoulos D J, Karabarbounis A, Margaritis L H. Mechanism for action of electromagnetic fields on cells. Biochemical and Biophysical Research Communications. 2002; 298(1):95-102.

Pawluk W, Turk Z, Fischer G, Kobinger W. Treatment of osteoarthritis with a new broadband PEMF signal. Presentation. 24th Annual Meeting of Bioelectromagnetics Society, Quebec City, Quebec, Canada, June 2002.

Pawluk, William, Magnetic Fields for Pain Control, Ch. 17 In Electromagnetic Fields in Biology and Medicine, CRC Press, publication January 2015. Marko S. Markov, Ed.

Pennington G M, Danley D L, Sumko M H et al. (February 1993) Pulsed, non-thermal, high-frequency electro-magnetic energy (DIAPULSE) in the treatment of grade I and grade II ankle sprains. MilMed 158(2): 101-104.

Picarelli H, Teixeira M J, de Andrade D C et al. (November 2010) Repetitive transcranial magnetic stimulation is efficacious as an add-on to pharmacological therapy in complex regional pain syndrome (CRPS) type I. J Pain 11(11): 1203-1210.

Pilla A A. (June 2013) Nonthermal electromagnetic fields: From first messenger to therapeutic applications. Electromagnet Biol Med 32(2): 123-136.

Pilla A A. Electromagnetic therapeutics: State-of-the-art in hard and soft tissue applications. Presentation. Fourth International Congress of European Bioelectromagnetics Assoc. (EBEA), Zagreb, Croatia, November 1998.

Pipitone N, Scott D L. (2001) Magnetic pulse treatment for knee osteoarthritis: A randomised, double-blind, placebo-controlled study. Curr Med Res Opin 17(3): 190-196.

Pleger B, Janssen F, Schwenkreis P et al. (Feb. 12, 2004) Repetitive transcranial magnetic stimulation of the motor cortex attenuates pain perception in complex regional pain syndrome type I. Neurosci Lett 356(2): 87-90.

Prato F S, Del Seppia C, Kavaliers M et al. Stress-induced analgesia in house mice and deer mice is reduced by application of various magnetic fields conditions. 21st Annual Meeting of Bioelectromagnetics Society, Long Beach, Calif., June 1999. Abstract 6-3:38

Prato F S, Thomas A W, Cook C M. (2001) Human standing balance is affected by exposure to pulsed ELF magnetic fields: Light intensity-dependent effects. Neuroreport 12(7): 1501-1505.

Preszler R R. A non-invasive complementary method of reducing chronic muscular low back pain using permanent magnetic therapy. Master thesis, Physician Assistant Studies, University of Nebraska School of Medicine, Physician Assistant Program, Lincoln, Omaha, Nebr., 2000.

Prusinski A, Wielka J, Durko A. (1987) Pulsating electromagnetic field in the therapy of headache. In Second Symposium on Magnetotherapy, Szekesfehervar, Hungary, May 1987. J Bioelectr 7(1): 127-128.

Pujol J, Pascual-Leone A, Dolz C et al. (1998) The effect of repetitive magnetic stimulation on localized musculoskeletal pain. Neuroreport 9(8): 1745-1748.

Punnonen R, Gronroos M, Luikko P et al. (1980) The use of pulsed high-frequency therapy (Curapuls) in gynecology and obstetrics. Acta Obstet Gynecol Scand 59(2): 187-188.

Randall C, Randall H, Dobbs F et al. (June 2000) Randomized controlled trial of nettle sting for treatment of base-of-thumb pain. J Royal Soc Med 93(6): 305-309.

Rauscher E, Van Bise W L. Pulsed magnetic field treatment of chronic back pain. 23rd Annual Meeting of Bioelectromagnetics Society, St. Paul, Minn., June 2001. Abstract 6-3:38

Reed M W, Bickerstaff D R, Hayne C R, Wyman A, Davies J. (June 1987) Pain relief after inguinal herniorrhaphy. Ineffectiveness of pulsed electromagnetic energy. Br J Clin Pract 41(6): 782-784.

Rehacek J, Straub J, Benova H. (1982) The effect of magnetic fields on coxarthroses. Fysiatr Revmatol Vestn 60(2): 66-68.

Richards T L, Lappin M S, Acosta-Urquidi J, Kraft G H, Heide A C, Lawrie F W, et al. Double-blind study of pulsing magnetic field effects on multiple sclerosis. J Altern Complement Med. 1997; 3(1):21-9.

Robertson J A, Théberge J, Weller J et al. (Mar. 6, 2010) Low-frequency pulsed electromagnetic field exposure can alter neuroprocessing in humans. J Royal Soc Interface 7(44): 467-473.

Rohde C, Chiang A, Adipoju O et al. (June 2010) Effects of pulsed electromagnetic fields on interleukin-1 beta and postoperative pain: A double-blind, placebo-controlled, pilot study in breast reduction patients. Plast Reconstr Surg 125(6): 1620-1629.

Roos H, Laurén M, Adalberth T et al. (April 1998) Knee osteoarthritis after meniscectomy: Prevalence of radiographic changes after twenty-one years, compared with matched controls. Arthritis Rheumatol 41(4): 687-693.

Sandyk R. Role of the pineal gland in multiple sclerosis: a hypothesis. Journal of Alternative & Complementary Medicine. 1997; 3(3):267-90.

Sartucci F, Bonfiglio L, Del Seppia C et al. (1997) Changes in pain perception and pain-related somatosensory evoked potentials in humans produced by exposure to oscillating magnetic fields. Brain Res 769(2): 362-366.

Saveriano G, Ricci S. (April 1989) Experiences in treating secondary post-traumatic algodystrophy with low-frequency PEMFs in conjunction with functional rehabilitation. In International Symposium in Honor of Luigi Galvani, Bologna, Italy. J Bioelectr 8(2): 320.

Schauble, M. K., Habal, M. B., and Gullick, H. D. Inhibition of Experimental Tumor Growth in Hamsters by Small Direct Currents. Arch. Pathol. Lab. Med. 101, 294-297 (1977).

Schroter M. (March/April 1976) Conservative treatment of 240 patients with magnetic field therapy. Medizinisch-Orthopadische Technik 2:78.

Segal N A, Toda Y, Huston J et al. (2001) Two configurations of static magnetic fields for treating rheumatoid arthritis of the knee: A double-blind clinical trial. Arch Phys Med Rehabil 82(10): 1453-1460.

Shafford H L, Hellyer P W, Crump K T et al. (2002) Use of a pulsed electromagnetic field for treatment of postoperative pain in dogs: A pilot study. Vet Anaesth Analg 29(1): 43-48.

Sharrard W. A double-blind trial of pulsed electromagnetic fields for delayed union of tibial fractures. Journal of Bone & Joint Surgery, British Volume. 1990 May 1, 1990; 72-B(3):347-55.

Sherman R A, Acosta N M, Robson L. (1999) Treatment of migraine with pulsing electromagnetic fields: A double-blind, placebo-controlled study. Headache 39(8): 567-575.

Shupak N M, McKay J C, Nielson W R et al. (2006) Exposure to a specific pulsed low-frequency magnetic field: A double-blind placebo-controlled study of effects on pain ratings in rheumatoid arthritis and fibromyalgia patients. Pain Res Manage 11(2): 85-90.

Shupak N M, Prato F S, Thomas A W. (Jun. 10, 2004) Human exposure to a specific pulsed magnetic field: Effects on thermal sensory and pain thresholds. Neurosci Lett 363(2): 157-162.

Smith, J., Romansky, N., Vomero, J. and Davis, R. H. The Effect of Electrical Stimulation on Wound Healing in Diabetic Mice. J. Amer. Podiatry Assoc. 74, 71-75 (1984).

Spadaro, J. A. Electrically Stimulated Bone Growth in Animals and Man. Clinical Orthopeds. and Rel. Res. 122, 325-332 (1977).

Spadaro, J. A., Chase, S. E. and Webster, D. A. Bacterial Inhibition by Electrical Activation of Percutaneous Implants. J. Biomed. Mat. Res. 20, 565-577 (1986).

Stewart D J, Stewart J E. (1989) The destabilization of an abnormal physiological balanced situation, chronic musculoskeletal pain, utilizing magnetic biological device. Acta Med Hung 46(4): 323-337.

Stiller M J, Pak G H, Shupack J L, Thaler S, Kenny C, Jondreau L. A portable pulsed electromagnetic field (PEMF) device to enhance healing of recalcitrant venous ulcers: a double-blind, placebo-controlled clinical trial. British Journal of Dermatology. 1992; 127(2):147-54.

Sutbeyaz S T, Sezer N, Koseoglu B F. (February 2006) The effect of pulsed electromagnetic fields in the treatment of cervical osteoarthritis: A randomized, double-blind, sham-controlled trial. Rheumatol Int 26(4): 320-324.

Sutbeyaz S T, Sezer N, Koseoglu B F. The effect of pulsed electromagnetic fields in the treatment of cervical osteoarthritis: a randomized, double-blind, sham-controlled trial. Rheumatol Int. 2006; 26(4):320-4.

Sutbeyaz S T, Sezer N, Koseoglu F et al. (October 2009) Low-frequency pulsed electromagnetic field therapy in fibromyalgia: A randomized, double-blind, sham-controlled clinical study. Clin J Pain 25(8): 722-728.

Takeshige C, Sato M. (April-June 1996) Comparisons of pain relief mechanisms between needling to the muscle, static magnetic field, external qigong and needling to the acupuncture point. Acupunct Electrother Res 21(2): 119-131.

Taverner M, Loughnan T. (February 2014) Transcutaneous pulsed radiofrequency treatment for patients with shoulder pain booked for surgery: A double-blind, randomized controlled trial. Pain Pract 14(2):101-108.

Tesic D, Djuric M, Pekaric-Nadj N et al. PEMF aided pain reduction in stomatology. 21st Annual Meeting of Bioelectromagnetics Society, Long Beach, Calif., June 1999. Abstract P-141:157.

Thamsborg G, Florescu A, Oturai P et al. (July 2005) Treatment of knee osteoarthritis with pulsed electromagnetic fields: A randomized, double-blind, placebo-controlled study. Osteoarthr Cartil 13(7):575-581.

Thomas A W, Drost D J, Prato F S. (2001) Human subjects exposed to a specific pulsed (200 uT) magnetic field: Effects on normal standing balance. Neurosci Lett 297(2): 121-124.

Thomas A W, Graham K, Prato F S et al. (Winter 2007) A randomized, double-blind, placebo-controlled clinical trial using a low-frequency magnetic field in the treatment of musculoskeletal chronic pain. Pain Res Manage 12(4): 249-258.

Thomas A W, Prato F S. Magnetic field based pain therapeutics and diagnostics. Presentation. 24th Annual Meeting of Bioelectromagnetics Society, Quebec City, Quebec, Canada, June 2002.

Thomas A W, White K P, Drost D J et al. (Aug. 17, 2001) A comparison of rheumatoid arthritis and fibromyalgia patients and healthy controls exposed to a pulsed (200 microT) magnetic field: Effects on normal standing balance. Neurosci Lett 309(1): 17-20.

Thomas D, Collins S, Strauss S. (March 1992) Somatic sympathetic vasomotor changes documented by medical thermographic imaging during acupuncture analgesia. Clin Rheumatol 11(1): 55-59.

Thuile C, Walzl M. (2002) Evaluation of electromagnetic fields in the treatment of pain in patients with lumbar radiculopathy or the whiplash syndrome. Neuro Rehabil 17:63-67.

Trock D H, Bollet A J, Dyer R H Jr et al. (March 1993) A double-blind trial of the clinical effects of pulsed electromagnetic fields in osteoarthritis. J Rheumatol 20(3): 456-460.

Trock D H, Bollet A J, Markoll R. (1994) The effect of pulsed electromagnetic fields in the treatment of osteoarthritis of the knee and cervical spine. Report of randomized, double blind, placebo controlled trials. J Rheumatol 21(10): 1903-1911.

Trock D H. (February 2000) Electromagnetic fields and magnets. Investigational treatment for musculoskeletal disorders. Rheum Dis Clin N Am 26(1): 51-62, viii.

Ugawa Y, Terao Y, Hanajima R et al. (September 1997) Magnetic stimulation over the cerebellum in patients with ataxia. Electroencephalogr Clin Neurophysiol 104(5): 453-458.

Uzunca K, Birtane M, Taştekin N. (January 2007) Effectiveness of pulsed electromagnetic field therapy in lateral epicondylitis. Clin Rheumatol 26(1): 69-74.

Vallbona C, Richards T. (August 1999) Evolution of magnetic therapy from alternative to traditional medicine. Phys Med Rehabil Clin N Am 10(3): 729-754.

Van Zundert J, Patijn J, Kessels A et al. (January 2007) Pulsed radiofrequency adjacent to the cervical dorsal root ganglion in chronic cervical radicular pain: A double blind sham controlled randomized clinical trial. Pain 127(1-2): 173-182.

Varani K, Gessi S, Merighi S, Iannotta V, Cattabriga E, Spisani S, et al. Effect of low frequency electromagnetic fields on A2A adenosine receptors in human neutrophils. British Journal of Pharmacology. 2002; 136(1):57-66.

Weadock, K., Olson, R. M. and Silver, F. H. Evaluation of Collagen Crosslinking Rechniques. Biomater. Med. Devices Artif. Organs. 11, 293-318 (1984).

Weintraub M I, Cole S P. (July-August 2008) A randomized controlled trial of the effects of a combination of static and dynamic magnetic fields on carpal tunnel syndrome. Pain Med 9(5): 493-504.

Weintraub M I, Herrmann D N, Smith A G et al. (July 2009) Pulsed electromagnetic fields to reduce diabetic neuropathic pain and stimulate neuronal repair: A randomized controlled trial. Arch Phys Med Rehabil 90(7): 1102-1109.

Wolcott, L. E., Wheeler, P. C., Hardwicke, H. M. and Rowley, B. A. Accelerated Healing of Skin by Electrotherapy: Preliminary Clinical Results. Southern Med. 62, 795-801 (1969).

Wong J Y, Rapson L M. (August 1999) Acupuncture in the management of pain of musculoskeletal and neurologic origin. Phys Med Rehabil Clin N Am 10(3): 531-545, vii-viii.

Wróbel M P, Szymborska-Kajanek A, Wystrychowski G et al. (September 2008) Impact of low frequency pulsed magnetic fields on pain intensity, quality of life and sleep disturbances in patients with painful diabetic polyneuropathy. Diabetes Metab 34(4 Pt 1): 349-354.

Wu, K. T., Go, N., Dennis, C., Enquist, I. F. and Sawyer, P. N. Effects of Electric Currents and Interfacial Potentials on Wound Healing. J. Surg. Res. 7, 122-128 (1967).

Yannas, I. V. and Burke, J. F. Design of an Artificial Skin. I. Basic design principles. J. Biomed. Mater. Res. 14, 65-81, (1980).

Yoo M, Cho Y, Kim K, Chun Y, Chung C. Pulsed Electromagnetic Fields Treatment For The Early Stages Of Osteonecrosis Of The Femoral Head. Journal of Bone & Joint Surgery, British Volume. 2004 Feb. 1, 2004; 86-B (Supp. II):148-9.

Zimmerman, M., Parsons, J. R., Alexander, H. and Weiss, A. B. The Electrical Stimulation of Bone Using a Filamentons Carbon Cathode. J. Biomed. Mat. Res. 18, 927-938 (1984).

Zorzi C, Dall'Oca C, Cadossi R et al. (July 2007) Effects of pulsed electromagnetic fields on patients' recovery after arthroscopic surgery: Prospective, randomized and double-blind study. Knee Surg Sports Traumatol Arthrosc 15(7): 830-834

See, U.S. Pat. Nos. 2,400,316; 2,497,164; 2,648,727; 3,043,310; 3,181,535; 3,270,746; 3,329,148; 3,329,149; 3,658,051; 3,797,500; 3,800,802; 3,820,888; 3,890,953; 3,893,462; 3,902,502; 3,915,151; 3,952,751; 3,978,864; 4,028,518; 4,095,588; 4,105,017; 4,128,824; 4,177,796; 4,197,851; 4,233,965; 4,266,532; 4,305,115; 4,315,503; 4,338,945; 4,340,063; 4,374,482; 4,428,366; 4,454,882; 4,461,300; 4,479,388; 4,548,208; 4,550,714; 4,556,051; 4,586,509; 4,616,629; 4,627,438; 4,641,633; 4,654,574; 4,672,951; 4,674,482; 4,765,310; 4,793,325; 4,829,984; 4,850,372; 4,889,526; 4,911,686; 4,926,881; 4,937,323; 4,940,453; 4,942,880; 4,993,413; 4,998,532; 5,000,000; 5,000,178; 5,001,000; 5,008,561; 5,014,699; 5,058,582; 5,116,304; 5,123,898; 5,147,284; 5,181,902; 5,195,941; 5,224,922; 5,269,747; 5,273,033; 5,314,401; 5,338,286; 5,351,389; 5,370,680; 5,386,837; 5,401,233; 5,407,421; 5,441,495; 5,441,527; 5,478,303; 5,480,373; 5,514,175; 5,518,496; 5,529,569; 5,565,005; 5,584,863; 5,595,564; 5,703,735; 5,707,334; 5,718,246; 5,718,721; 5,723,001; 5,743,844; 5,766,231; 5,778,894; 5,792,209; 5,814,078; 5,877,627; 5,908,444; 5,951,459; 5,960,500; 5,960,513; 5,968,527; 5,983,134; 5,990,177; 5,997,464; 6,004,257; 6,011,994; 6,024,691; 6,029,084; 6,048,302; 6,075,603; 6,083,149; 6,086,525; 6,087,652; 6,099,459; 6,132,361; 6,132,362; 6,149,577; 6,155,966; 6,169,963; 6,174,276; 6,179,772; 6,186,941; 6,190,893; 6,200,259; 6,213,934; 6,217,604; 6,231,187; 6,231,528; 6,234,953; 6,246,912; 6,261,221; 6,261,831; 6,285,514; 6,301,506; 6,321,119; 6,321,120; 6,334,069; 6,348,070; 6,371,905; 6,418,345; 6,421,562; 6,424,863; 6,425,852; 6,434,426; 6,443,883; 6,450,941; 6,458,151; 6,458,157; 6,463,336; 6,535,767; 6,556,872; 6,560,489; 6,561,968; 6,564,093; 6,569,654; 6,589,159; 6,629,971; 6,647,301; 6,648,812; 6,652,473; 6,675,047; 6,678,562; 6,684,108; 6,701,185; 6,819,210; 6,839,589; 6,839,595; 6,844,378; 6,853,864; 6,856,839; 6,895,282; 6,919,205; 6,934,580; 6,955,642; 6,995,013; 7,010,353; 7,022,506; 7,039,467; 7,089,060; 7,113,830; 7,117,034; 7,130,692; 7,158,835; 7,160,241; 7,162,303; 7,167,753; 7,175,587; 7,177,695; 7,177,696; 7,215,995; 7,228,178; 7,280,861; 7,288,062; 7,333,858; 7,354,393; 7,354,748; 7,361,136; 7,367,988; 7,374,916; 7,419,474; 7,429,471; 7,456,189; 7,465,546; 7,465,566; 7,468,264; 7,507,198; 7,513,906; 7,517,311; 7,520,849; 7,551,957; 7,563,224; 7,564,267; 7,566,295; 7,587,230; 7,602,218; 7,617,005; 7,620,451; 7,647,115; 7,653,438; 7,659,750; 7,662,615; 7,696,860; 7,717,948; 7,740,574; 7,744,524; 7,744,869; 7,758,490; 7,768,338; 7,783,348; 7,797,552; 7,819,794; 7,829,535; 7,840,272; 7,842,432; 7,867,235; 7,896,797; 7,937,143; 7,939,218; 7,981,611; 7,988,613; 8,014,846; 8,017,369; 8,029,432; 8,039,031; 8,060,210; 8,065,015; 8,070,703; 8,079,966; 8,131,371; 8,131,372; 8,142,774; 8,145,316; 8,145,317; 8,150,518; 8,150,519; 8,150,520; 8,167,784; 8,175,711; 8,292,834; 8,313,908; 8,343,027; 8,346,367; 8,347,891; 8,376,925; 8,412,328; 8,412,346; 8,415,123; 8,430,805; 8,433,423; 8,435,166; 8,444,640; 8,454,543; 8,454,594; 8,460,167; 8,477,003; 8,478,422; 8,548,600; 8,551,069; 8,560,077; 8,569,050; 8,571,642; 8,600,514; 8,620,423; 8,626,300; 8,657,732; 8,682,448; 8,684,998; 8,721,637; 8,728,137; 8,728,138; 8,740,896; 8,768,454; 8,768,470; 8,771,252; 8,774,913; 8,774,922; 8,775,340; 8,784,463; 8,785,196; 8,795,147; 8,805,521; 8,805,545; 8,818,514; 8,827,886; 8,845,629; 8,852,163; 8,880,186; 8,906,659; 8,911,342; 8,932,196; 8,934,978; 8,936,560; 8,936,804; 8,948,865; 8,958,871; 8,961,385; 8,968,172; 8,972,024; 8,979,727; 8,980,851; 8,983,595; 8,986,294; 8,998,791; 9,002,477; 9,005,102; 9,023,037; 9,072,527; 9,108,040; 9,119,829; 9,125,661; 9,131,978; 9,138,281; 9,186,198; 9,186,213; 9,186,514; 9,192,715; 9,198,792; 9,215,788; 9,232,986; 9,245,675; 9,265,558; 9,265,794; 9,278,231; 9,289,255; 9,289,618; 9,308,043; 9,308,044; 9,314,363; 9,314,630; 9,320,561; 9,320,913; 9,321,662; 9,326,817; 9,327,115; 9,327,119; 9,327,122; 9,327,136; 9,339,641; 9,345,909; 9,351,790; 9,352,002; 9,359,233; 9,364,267; 9,364,280; 9,387,338; 9,387,339; 9,393,144; 9,402,992; 9,415,233; 9,421,357; 9,421,370; 9,427,598; 9,404,449; 9,411,030; 9,415,233; 9,421,357; 9,421,370; 9,427,598; 9,433,629; 9,433,682; 9,433,797; 9,439,726; 9,440,089; 9,445,867; 9,452,297; 9,456,869; 9,463,066; 9,468,497; 9,474,563; 9,480,991; 9,486,270; 9,486,638; 9,498,491; 9,498,638; 9,498,639; 9,510,931; 9,526,918; 9,532,832; 9,554,935; 9,556,243; 9,603,637; 9,610,443; 9,610,459; 9,612,308; 9,630,001; 9,630,004; 9,636,174; 9,656,096; 9,662,183; 9,669,074; 9,675,413; 9,684,074; 9,694,193; 9,694,194; 9,707,035; 9,724,308; 9,724,534; 9,726,738; 9,727,764; 9,730,946; 9,731,132; 9,735,629; 9,743,983; 9,746,407; 9,757,192; 9,757,193; 9,757,583; 9,757,584; 9,758,806; 9,776,014; 9,795,500; 9,796,609; 9,801,905; D762,864; D763,453; D706,432; RE41,391; 20010007937; 20010027278; 20010031906; 20010031986; 20010041820; 20010044643; 20020022863; 20020034796; 20020035358; 20020052634; 20020086842; 20020091850; 20020147380; 20020165583; 20030018368; 20030023283; 20030028072; 20030050527; 20030083537; 20030093028; 20030095022; 20030099979; 20030125661; 20030125769; 20030130709; 20030158583; 20030158585; 20030163168; 20030171640; 20030176895; 20030181791; 20030195594; 20030211084; 20040005297; 20040006373; 20040054379; 20040073260; 20040073269; 20040077923; 20040106843; 20040122281; 20040138709; 20040138722; 20040176803; 20040176805; 20040176806; 20040210254; 20040230224; 20040241311; 20040267333; 20047744524; 20050005120; 20050049640; 20050059153; 20050065394; 20050084962; 20050124847; 20050134265; 20050148807; 20050154426; 20050165460; 20050177203; 20050182287; 20050187423; 20050197522; 20050198812; 20050215842; 20050222625; 20050228209; 20050251229; 20050259373; 20050267355; 20050288744; 20057740574; 20057758490; 20060009825; 20060024822; 20060030896; 20060030906; 20060051328; 20060057693; 20060085049; 20060094112; 20060094924; 20060129022; 20060161226; 20060190043; 20060205993; 20060206174; 20060212077; 20060235473; 20060240316; 20060245217; 20060258896; 20060271131; 20060293724; 20070014055; 20070021645; 20070026514; 20070027355; 20070030176; 20070038252;

20070039211; 20070043254; 20070060477; 20070060954; 20070060981; 20070065420; 20070078292; 20070104694; 20070105769; 20070139167; 20070149901; 20070173904; 20070203389; 20070203390; 20070208249; 20070208385; 20070212538; 20070282156; 20070288072; 20070299472; 20080015463; 20080021327; 20080039901; 20080058793; 20080077193; 20080092435; 20080097142; 20080125617; 20080132971; 20080140155; 20080200749; 20080208284; 20080208287; 20080215113; 20080215116; 20080217263; 20080228185; 20080269838; 20080280169; 20080280826; 20080287730; 20080288035; 20080294269; 20080306325; 20090018613; 20090030476; 20090043188; 20090062885; 20090099623; 20090104160; 20090105781; 20090131739; 20090132010; 20090156884; 20090163762; 20090206882; 20090206883; 20090206907; 20090216068; 20090227829; 20090227831; 20090234179; 20090234417; 20090240310; 20090287126; 20090326315; 20090326602; 20100004500; 20100005571; 20100010288; 20100049262; 20100057655; 20100075211; 20100082079; 20100121407; 20100160712; 20100160999; 20100168501; 20100179373; 20100185041; 20100197993; 20100204538; 20100210893; 20100221346; 20100222629; 20100222631; 20100239544; 20100262052; 20100298624; 20110004261; 20110021863; 20110065976; 20110065977; 20110105959; 20110112352; 20110112522; 20110118852; 20110124717; 20110130618; 20110152598; 20110160811; 20110184223; 20110190849; 20110207989; 20110213195; 20110217775; 20110224480; 20110282412; 20110288611; 20110295339; 20120016442; 20120038441; 20120059287; 20120078328; 20120089201; 20120101327; 20120101544; 20120116149; 20120135390; 20120135392; 20120143285; 20120149968; 20120172653; 20120184800; 20120215281; 20120245403; 20120253101; 20120265048; 20120302821; 20120316482; 20120330090; 20130013339; 20130035539; 20130072746; 20130085317; 20130158456; 20130158634; 20130165829; 20130171094; 20130178425; 20130218235; 20130238061; 20130238062; 20130245358; 20130261374; 20130267003; 20130267020; 20130274540; 20130288260; 20130289416; 20130293327; 20130296940; 20130317282; 20130344559; 20140023983; 20140024882; 20140046115; 20140046117; 20140046232; 20140046423; 20140066837; 20140081070; 20140114382; 20140148870; 20140155799; 20140163304; 20140207018; 20140207040; 20140207041; 20140213843; 20140213844; 20140221726; 20140228620; 20140249354; 20140249355; 20140303425; 20140322292; 20140342300; 20140342428; 20140343642; 20140350649; 20150005672; 20150010499; 20150025299; 20150094521; 20150099804; 20150107774; 20150141736; 20150151136; 20150174166; 20150196771; 20150202454; 20150217107; 20150217125; 20150217126; 20150258346; 20150273221; 20150297910; 20150306412; 20150315539; 20150320697; 20150328033; 20150328034; 20150328476; 20150342661; 20160000870; 20160008024; 20160015432; 20160015545; 20160022989; 20160038753; 20160051827; 20160067103; 20160067515; 20160067517; 20160074670; 20160074671; 20160121135; 20160129273; 20160129274; 20160129284; 20160145571; 20160151416; 20160151646; 20160193466; 20160206876; 20160228721; 20160228723; 20160235983; 20160246944; 20160306042; 20160313159; 20160317828; 20160331990; 20160339261; 20160346016; 20160346561; 20160354446; 20160372362; 20170000536; 20170001025; 20170001201; 20170027858; 20170028184; 20170030188; 20170039404; 20170043177; 20170050019; 20170056644; 20170071977; 20170072210; 20170080245; 20170087367; 20170113059; 20170113060; 20170128538; 20170151442; 20170152500; 20170157318; 20170165496; 20170173076; 20170173295; 20170173347; 20170202509; 20170209717; 20170225005; 20170226463; 20170246481; 20170252574; 20170266443; 20170266458; 20170266459; 20170291039; 20170295778; 20170298340; 20170298341; 20170304642; 20170319250; EP1216076; WO0115774; WO0209811; WO2004108208; WO2005051306; WO2008070001; WO2009155516; WO2010067336; WO2010149164; WO2011053607; WO8301742; WO9527533; WO9611723; WO9632158;

SUMMARY OF THE INVENTION

A system and method is provided for applying a low strength, low frequency magnetic field therapy to biological tissues.

A low frequency oscillating current is passed through a coil configured to induce a magnetic field strength of about 0.01-5 mTesla at a distance of 1 cm from the coil (or a cover over the coil), at a pulse frequency within the range 0.5-1,000 Hz, and more generally 5-1,000 Hz, for example at 100 Hz. The coil is e.g., 5-200 turns, having a diameter of 2-20 mm, of 0.2 mm copper wire, with a hollow core.

With each rising and falling edge of a pulse (e.g., square wave), the inductor coil establishes a magnetic field that oscillates with a frequency spectrum that is dependent on the risetime and falltime of the pulse. A pulse occurs with each transition (edge of the square wave), of alternating polarity. The circuit acts as a filter, and with a quality audio amplifier with sufficient headroom driving the circuit, the pulses will contain strong frequency components at 10-24 kHz. Thus, the signal emitted from the coil will typically be a low frequency square wave magnetic field at the pulse edge rate, i.e., double the 0.5-1,000 Hz pulse rate, and a high frequency emission that may be an underdamped oscillation, overdamped oscillation, or critically damped oscillation within the decay period that accompanies each edge transition, dependent on the amplifier and circuit components. Due to the power storage in the inductive coil and capacitor during excitation with the square wave, the peak power of the damped oscillation is not directly related to the power output capacity of the audio amplifier that drives the circuit, though the average power will generally be so limited.

Typically, the sharper the edge of the pulse, the greater the high frequency components in the electrical signal. With a quality audio amplifier driven by a digital to analog converter designed for digital audio sources, the frequency range may be flat (e.g., <3 dB rolloff) to >20 kHz, with a digital sampling rate of ~44.1 kHz (or in some cases, 196 kHz). However, in such audio circuits, the digital source typically exceeds the bandwidth of the analog signal, and the typical audio range extends to about 20 kHz, so the amplifier may have a low pass filter (smoothing filter) which reduces "digital noise" above 20 kHz. The current is preferably controlled by a smartphone or other programmable device, and may be provided through an audio jack or other mechanical electronics connector. Alternately, a digital interface and/or wireless interface may control the current. An app on the smartphone may be used to control the frequency, amplitude/envelope modulation, waveform, duration, etc. of the oscillation. The coil may be in mineral or plastic housing with a simple filter, and TRRS-type audio jack.

A circuit may be provided which resonates, e.g., at a frequency below 100 kHz, and in particular which causes a ringing upon abrupt change in a voltage applied to the circuit. Thus, a pulse train (symmetric or asymmetric) may be received by the device comprising the circuit and the coil, which is excited by the pulses, and resonates with a decay upon each transition. Typically the circuit is passive, but in some embodiments, it contains diodes, transistors, integrated circuits, or the like. For example, some audio amplifiers may seek to damp the ringing within the circuit, and therefore it may be advantageous to include active or passive edge sharpening electronics within the device, which can be achieved through use of semiconductors, e.g., a digital control or analog devices that have nonlinear transfer functions and those that act as "triggers".

There is an emerging trend to eliminate an audio amplifier within a smartphone, which is replaced with a wireless interface (e.g., Bluetooth) or a wired interface. Therefore, while a passive device is currently preferred for use with smartphones or other programmable devices that have their own analog audio interface, the technology may also be used with active circuits that internally generate the excitation for the coil. However, while the device can autonomously generate the pulsed electromagnetic field (PEMF) therapy, it is preferred that the controlling device be connected to an on-line communications network for upload of feedback, user input, and sensor data, and download of therapy plans and excitation parameters. Therefore, one aspect of the technology is to provide a PEMF device that is part of the "Internet of Things". However, because of the possibility of interference between the communications of the device and the therapy to be administered, in a preferred embodiment, communications are not concurrent with therapy. This, however, may be dependent on a number of factors, and is not a required attribute in all cases.

The smartphone may control the device to apply a therapy according to various theories. The device is not limited to any particular set of excitation parameters, and indeed a particular advantage is that a therapist can design different regimens using the same system. Likewise, while this is not required, the smartphone provides a convenient means for patient feedback, and may thus permit an adaptive therapy. In the case of acute pain relief, the smartphone may employ a genetic algorithm to explore various treatment parameters, seeking for a particular patient the optimum, which may vary over time. A remote server may receive feedback (which may be anonymized in some cases), allowing the various states of the genetic algorithm to be tested over a large population, which can therefore reveal patient subpopulations and groups, and expand the testing space to a degree larger than possible with a single patient.

It is preferred that, if the smartphone is in close proximity to the patient at the time of therapy, that the therapy be applied with the smartphone in "airplane mode", that is, with radio frequency communications from the phone deactivated. This will avoid exposing the patient to potentially harmful high frequency waves during the therapy. Therefore, required remote communications are buffered for transmission after the therapy is concluded. Likewise, any required parameter downloads must be complete prior to initiation of therapy.

The coil is advantageously disposed within a spherical housing, which may have a bored cylindrical hole for the coil, and an electrical connector extending therefrom. Based on current technologies, a 3.5 mm phono jack or TRRS jack is available on many smartphone. However, some devices do not have this interface available. Therefore, another available interface may be used, such as a wired digital interface, such as USB (2, 3, 3.1, etc.), Thunderbolt, etc., and wireless interfaces, such as WiFi, Bluetooth, NFC, Zigbee, Zwave, etc.

The device does not need a smartphone or other standard intelligent/programmable consumer device, and for example, may be driven by an internal microcontroller, AM or FM radio receiver, analog or digital circuitry, etc. However, a smartphone is advantageous because it permits relatively easy programming, and remote communications as may be appropriate. Note that as technologies advance, the form factor and suite of functionality in a "smartphone" may evolve. Since the PEMF therapy is not dependent on the phone per se, any device that suitably generates excitation for the coil, and accepts and responds to control parameters for generating the PEMF, may be used. According to present availability and ubiquity of smartphones and tablets, e.g., Android, Apple, Windows (e.g., mobile), Linux, Chrome, Blackberry OS, etc., this type of platform is convenient, capable and preferred.

It is therefore an object to provide a magnetic field therapy device, comprising: a conductive coil fed with a current, to supply a therapy to a tissue, the therapy comprising a magnetic field strength below 50 mT, preferably below 25 mT, more preferably below 10 mT, and most preferably below 5 mT, and may have a strength as low as 0.01 mT max. Preferably, the field penetrates into the tissue at least 1 cm.

The coil may be, for example, a single layer of between 5 and 200 turns, e.g., 0.2 mm copper wire, having an external diameter of between about 2 mm and 20 mm.

The excitation received by the circuit which excites the coil, may be an oscillating electrical signal having a frequency range from about 5 Hz to about 100 kHz.

The circuit may present an impedance of at least 8 Ohms at 100 Hz to a driver circuit.

The signal which drives the circuit may have a slew rate of ~10 kHz, e.g., 1 V/100 $\mu$S=$10^5$ V/sec, and the circuit may have a nominal load impedance of 33$\Omega$ for signals having that slew rate.

The coil (and optionally circuit) may be contained within a housing, such as a spherical magnetically impermeable material, such as a mineral (natural or synthetic), polymer, or non-magnetic metal. The housing is configured to contact the skin, and thus permit a therapy of the tissues underneath the skin.

A filter may be provided, optionally within the housing, having at least one pole within a range of 5 Hz to 50,000 Hz, configured to filter the oscillating electrical signal supplied to the conductive coil. The filter may resonate upon transient changes in voltage. The filter may have a pole at about 3 kHz.

The conductive coil may have a diameter of about 5-10 or 10-12 mm, and preferably about 6-8 mm. The conductive coil may have a diameter of less than about 15 or 12 mm. The size and shape of the coil are governed by the laws of physics with respect to the magnetic field shape and strength. Thus, a deeper field typically requires a larger coil, which will require a higher current. If the coil is to be driven from an audio earphone jack amplifier, the maximum power available will be <200 mW, and typically <100 mW, corresponding to 1 V max into >8 Ohms. For example, with a 33 Ohm load resistor in the circuit, and a 1 V peak driven signal, the available average power will be about 30 mW. The presented impedance may be at least 30 Ohms.

The oscillating electrical signal may have a frequency range comprising 50 Hz. That is, the signal may assume a 50 Hz frequency, or be a broadband signal encompassing 50 Hz.

The cover may have a spherical surface having a diameter of about 15-30 mm preferably 20-25 mm, and most preferably 20 mm.

The cover may be formed of a magnetically impermeable mineral, such as quartz.

The input may comprise an analog phono jack, such as a 3.5 mm TRRS phono jack.

The input may also comprise a digital audio connector.

The filter may comprise a circuit board having at least one resistor and at least one capacitor.

The input may comprise a radio frequency receiver, the magnetic field therapy device further comprising a self-contained battery power source to power the radio frequency receiver and the conductive coil.

The input may be adapted to receive a signal from a smartphone. The smartphone may be configured to generate the oscillating electrical signal based on a downloadable app which executes under a smartphone operating system. The smartphone may be configured to execute the downloadable app in airplane mode, substantially without emission of radio frequency signals in excess of 25 MHz.

It is also an object to provide a magnetic field therapy method, comprising: providing a conductive coil, an input configured to receive an oscillating electrical signal and to supply a current to the conductive coil, to thereby generate an oscillating magnetic field surrounding the conductive coil, and a cover, surrounding the conductive coil and the filter, adapted to contact human or animal skin and pass the oscillating magnetic field substantially without distortion or attenuation; generating the oscillating electrical signal in a first state with a smartphone under control of a smartphone app; and emitting the generated oscillating magnetic field surrounding the conductive coil into the human or animal skin adjacent to the cover, at a magnetic field strength of at least 0.01 mTesla at a distance of 1 cm from the cover. The method may further comprise receiving a user input to the smartphone; and generating the oscillating electrical signal in a second state with the smartphone under control of the smartphone app, the second state comprising a different distribution of frequencies of the oscillating electrical signal than the first state.

Under excitation by the oscillating electrical signal at a voltage of 1 V peak-to-peak, a magnetic field of between 0.01 mTesla and 5 mTesla may be obtained within a human or animal tissue under the human or animal skin contacting a surface of the cover at a depth of 1 cm from the surface of the cover, aligned with an axis of the conductive coil.

An electrical filter may be provided within the cover. The electrical filter may comprise a circuit board having at least one resistor and at least one capacitor. The filter may have a pole at about 3 kHz.

The conductive coil may have an inner diameter of about 8 mm. The presented impedance at the input may be at least 30 Ohms, e.g., having a 33Ω resistor in series with the coil. This value is dependent on typical smartphone audio amplifier designs, and a 33Ω load impedance at 10 kHz is typically acceptable for such amplifiers in common devices. Of course, with a particular device, the value of the load impedance (and thus the amount of power that is available for the PEMF) can vary.

The oscillating electrical signal may have a frequency range comprising 50 Hz.

The cover may comprise a spherical section having a diameter of about 2 cm. The cover may be formed of a magnetically impermeable mineral.

The method may further comprise generating, on a display of the smartphone, an indication of at least a direction in which the cover should be moved over the human or animal skin.

The magnetic field excited for a 100 Hz oscillating electrical signal at a voltage of 1 V peak-to-peak may be at least 0.05 mTesla at a depth of 1 cm in the human or animal tissue beneath the human or animal skin contacting the surface of the cover.

The input may comprise an analog phono jack or a digital audio connector.

The input may comprise a radio receiver, and the magnetic field therapy device may further comprise a self-contained battery power source to power the radio receiver and the current to the conductive coil.

The smartphone may execute the downloadable app in airplane mode, substantially without emission of radio frequency signals in excess of 25 MHz.

The oscillating electrical signal may be a square wave signal.

The circuit within the device may, for example, have a non-linear transfer function semiconductor device which conducts or triggers in a voltage dependent manner, and therefore generates high frequency signal components from a signal transition. For example, a diode "turns on" at 0.3-0.6 V in forward conduction (depending on junction composition). A pair of back-to-back diodes thus would be operative for "edge sharpening" for both rising and falling pulses. Similarly, a bipolar transistor/JFET/FET circuit may provide greater control over the conduction threshold and frequency characteristics. Other types of semiconductor devices may also be used in a passive circuit.

The circuit may also contain an active semiconductor device. For example, the power in the audio signal may be harvested with a rectifier circuit (preferably germanium or Schottky diodes or FETs, due to the low operating voltages) and stored on a capacitor, which is then used to run the active circuit. A voltage multiplier or step-up circuit may be employed as appropriate. A separate power source may also be provided, independent of the audio signal Note that the pulse signal is typically a square wave, but in practice, this need not have a symmetric duty cycle. Preferably, the spacing between upswing and downswing of the pulses is greater than the settling time of the coil and capacitor circuit, though in some cases, it may be shorter, allowing a relatively continuous excitation of the magnetic field therapy. All characteristics of the excitation signal may be controlled within the digital parameters of the control circuit and the analog characteristics of the amplifier and other circuit components, under control of the software in the smartphone or other control device.

It is also an object to provide a method of treating a human or animal, comprising: providing a smartphone having a magnetically actuated acoustic speaker; placing the speaker proximate to skin; generating an acoustic emission from the acoustic speaker and an accompanying magnetic emission, within a frequency range of 10 Hz-1000 Hz, controlled with a downloadable application for the smartphone; receiving user feedback into the smartphone downloadable application representing a subjective therapeutic effect; and modifying the acoustic emission based on the feedback.

It is a further object to provide a method of treating a human or animal, comprising: providing a smartphone having an electromagnetic vibration motor; placing the electromagnetic vibration motor proximate to skin; generating a vibration from the electromagnetic vibration motor and an accompanying magnetic emission, controlled with a downloadable application for the smartphone; receiving user feedback into the smartphone downloadable application representing a subjective therapeutic effect; and modifying the vibration based on the feedback.

It is another object to provide a pulsed electromagnetic field therapy device, comprising: an interface configured to receive an oscillating electrical signal from a programmable device; a coiled conductor, having at least 5 turns, and an inner diameter of between about 4-15 mm; a magnetically impermeable cover, having an outer surface configured for contact with human or animal skin; and a circuit within the magnetically impermeable cover, configured to excite the coiled conductor with a current corresponding to the oscillating electrical signal, to generate a magnetic field of between about 10 µTesla and 5 mTesla at a distance of 1 cm from the cover at a position axially aligned with the coiled conductor.

The interface may comprise an analog audio interface, presenting an impedance of between about 8-100 Ohms. The coiled conductor may comprise copper wire. The circuit may comprise a resistor and a capacitor.

The magnetically permeable cover may comprise a natural or synthetic mineral.

The pulsed electromagnetic field therapy device may further comprise a light emitting diode configured to illuminate in an emission pattern corresponding to an amplitude of the oscillating electric signal.

The interface may comprise a Bluetooth, WiFi, Zigbee, Zwave, or Near Field Communication protocol receiver.

The interface may comprise a 3.5 mm headphone jack analog audio interface, presenting an impedance of between about 8-100 Ohms.

The interface may comprise a microphone.

The circuit may comprise a capacitor in series with the coiled conductor.

It is another object to provide a pulsed electromagnetic field therapy method, comprising: receiving a pulse train from a programmable device, having a pulse frequency of between 5-1,000 Hz; passing a current corresponding to the pulse train through a coiled conductor having an inner diameter of between about 4-15 mm, within a cover configured to contact an exposed surface of a subject; emitting a pulse electromagnetic field from the coiled conductor corresponding to the current, having a maximum field strength of between about 10 µTesla and 5 mTesla at a distance of 1 cm from the cover at a position axially aligned with the coil coiled conductor, to thereby apply a pulsed electromagnetic field therapy to the subject.

The programmable device may comprise a mobile telecommunication device having an application program downloaded through a telecommunication port, the application program controlling an audio interface of the mobile telecommunication device to generate the pulse train, and controlling a user interface of the mobile telecommunication device to receive user input to at least initiate generation of the pulse train.

The method may further comprise receiving feedback from the subject relating to an effect of the pulsed electromagnetic field therapy.

The method may further comprise communicating a signal corresponding to the feedback from the mobile telecommunication device to a remote server through a communication network.

The method may further comprise receiving from the remote server a set of parameters for controlling generation of the pulse train. The set of parameters may comprise a pulse train frequency, and a pulse train duration.

The electromagnetic field therapy may comprise a resonant discharge of stored energy from the coiled conductor.

The passing a current corresponding to the pulse train through a coiled conductor may comprise passing the current through a capacitor and the coiled conductor.

The cover may have a spherical surface. The spherical surface may have a diameter of between 15 and 25 mm, e.g., about 20 mm.

The power for emission of the pulsed electromagnetic field therapy may be derived from the received pulse train or from a self-contained power source distinct from the pulse train.

The method may further comprise producing an optical signal when the pulsed electromagnetic therapy is in progress. The power for generating the optical signal may be derived from the received pulse train or a self-contained power source distinct from the pulse train. The pulse train may be received wirelessly. The pulse train may be received through a Bluetooth, WiFi, or NFC receiver, or an analog headphone jack, presenting a load of at least 30 Ohms, for example. The pulse train may also be received as an acoustic communication through a microphone.

The programmable device may generate an analog output having a plurality of different programmable sampling rates, further comprising selecting a sampling rate to alter the pulsed electromagnetic field therapy. The plurality of different programmable sampling rates comprise 44.1 kHz, 48 kHz, and 96 kHz. The pulse train may be a square wave pulse train. The pulse train may have a symmetric or asymmetric duty cycle.

It is a further object to provide a pulsed electromagnetic field therapy method, comprising: receiving a pulse signal from a programmable device, having a pulse repetition rate of between 5-1,000 pulses per second; passing a current corresponding to the pulse train through a coiled conductor having an inner diameter of between about 4-15 mm, within a cover configured to contact an exposed surface of a subject, the current having an asymmetric rise and fall; and emitting a pulse electromagnetic field from the coiled conductor corresponding to the current, having a maximum field strength of between about 10 µTesla and 5 mTesla at a distance of 1 cm from the cover at a position axially aligned with the coil coiled conductor, to thereby apply a pulsed electromagnetic field therapy to the subject.

It is another object to provide a magnetic field therapy device, comprising: a conductive coil having a diameter of between about 8 mm and 15 mm and having between 5-1000 turns; an analog input configured to receive an electrical signal from an analog audio interface device, a high pass filter; and a non-magnetic cover, surrounding the conductive coil and the filter, adapted separate the conductive coil from contact with an adjacent human or animal tissue substantially without disrupting a magnetic field emitted from the conductive coil, wherein under excitation by the electrical signal comprising square wave pulses at a frequency of 100 Hz and a voltage of 1 V peak-to-peak, a magnetic field of between 0.01 mTesla and 5 mTesla maximum is obtained at a distance of 1 cm from the cover.

The filter may comprise a resistor having a resistance of between about 10 Ohms and 100 Ohms, and a ceramic capacitor having a capacitance of about 1-50 µFarads, and the coiled conductor has between 5 and 200 turns.

DETAILED DESCRIPTION OF THE PREFERRED EMBODIMENTS

A preferred embodiment of the technology provides a small device that can be plugged into a standard headphone jack socket on any smartphone (Android or iPhone) and used with a downloaded software app.

A jackplug holder may also be provided so the device can be worn as a necklace when not in use. A keyring embodiment may also be provided.

Figure 1:
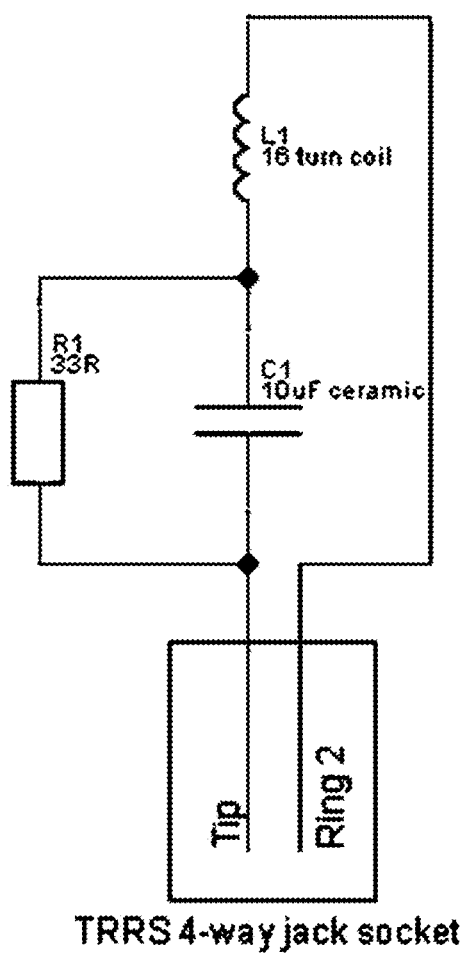
FIG. 1 shows a schematic of an electrical circuit according to the present invention.
Figure 2:
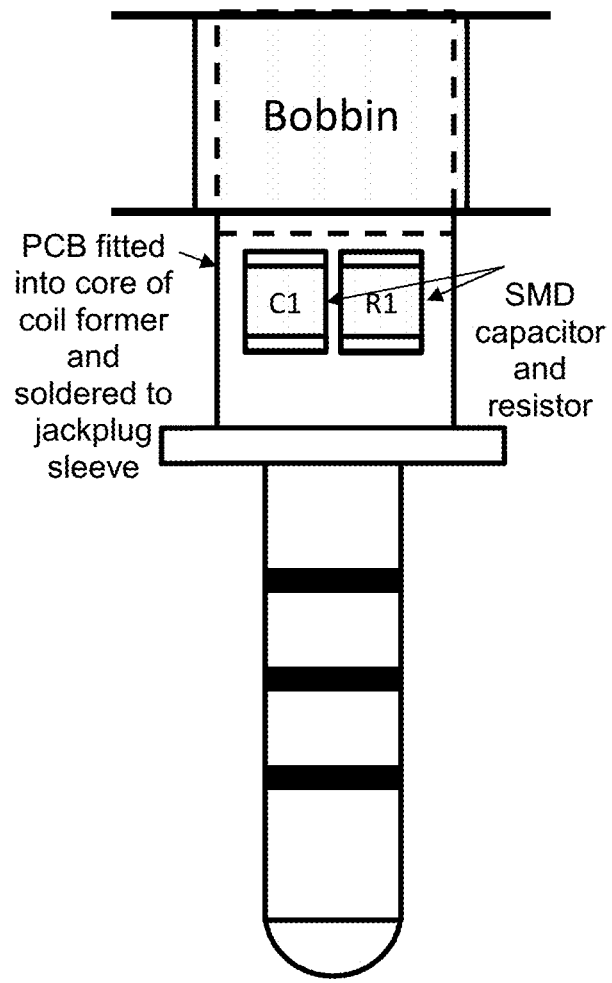
FIG. 2 shows a physical arrangement of a preferred embodiment of the invention.

The schematic is simple, consisting of 4 components, as shown in FIG. 1: A 16 turn (single layer) coil, 7.8-8 mm diameter, 0.2 mm enameled copper wire, on a P14 hollow core former (Farnell, 235-5082), in series with a 33 Ohm 0.1 W resistor in parallel with a 10 µF, >10 V ceramic capacitor (e.g., 1210 case, Farnell 249-7164). The resistor and capacitor are mounted to a 8-10 mm PCB (e.g., 0.6 mm FRP) soldered to the jackplug sleeve solder tag. The end of the coil and the resistor and capacitor are mounted on, and connected to the tip and ring 2 contacts of a 3.5 mm TRRS headphone jack. The coil is inserted into a 20 mm glass or mineral ball, such as a quartz sphere with a bored 8-10 mm dimeter, 15-18 mm deep cylindrical, glued or epoxied to the end of the TSSR jack (Lumberg 1532 02 Phone Audio Connector, Plug, 3.5 mm, 4 Contacts, Cable Mount, Plastic Body, Nickel Plated Contacts, Farnell 2101773). The arrangement is shown in FIG. 2.

The resistor and capacitor can be housed inside the bobbin to reduce total length of device.

The excitation through the headphone jack may be e.g., a 100 Hz square wave.

According to one theory, all frequencies used can be considered as musical tone frequencies when the all tones are tuned to the keynote 453.3 Hz—which is an important proton resonance. When more than one frequency is concurrently used, a musical chord may be generated. It is noted that it is unlikely that tissues respond to musical theory. However, the PEMF can excite afferent nerves and be communicated to the brain, which can then respond centrally or through efferent pathways.

The frequencies may have a symphonic quality, and as such need not be simple square waves, and rather may be arbitrary waveforms with dynamically changing frequencies.

The fundamental frequencies, in fact, may extend to 10 kHz, and perhaps beyond.

Figure 3:
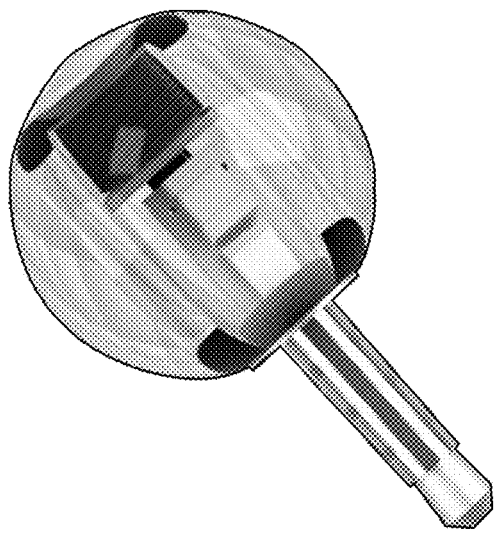
FIG. 3 shows an assembled view of a preferred embodiment of the invention with a spherical case.

FIG. 3 shows an assembled view of a preferred embodiment of the invention with a spherical case natural semi-transparent mineral case, showing the coil wound around a bobbin centrally located within the sphere, and a TRRS phono jack extending axially from the sphere. A mineral sphere (e.g., amethyst) was been found to be ergonomically and aesthetically acceptable, with respect to mass, thermal capacity (relevant to skin contact), magnetic characteristics, etc.

The device may be conveniently provided with a necklace-holder, which has a dummy TRRS socket to retain the device when not in use. The necklace provides a convenient way to carry and transport the device. A corresponding holder may be formed as a keyring, or the like.

Figure 4:
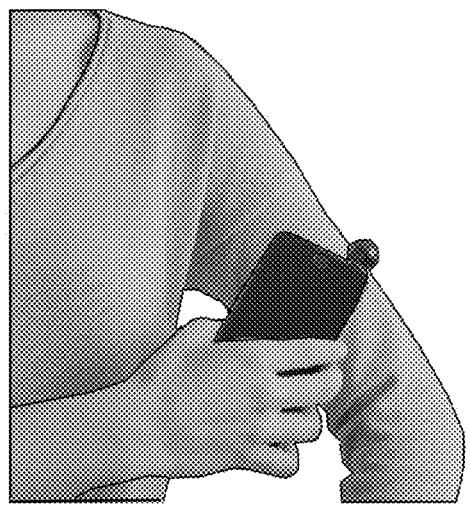
FIG. 4 shows an example of the device, plugged into a headphone jack of a smartphone, being used to apply a therapy to an upper arm region.

FIG. 4 shows an example of the device, in use, plugged in to the headphone jack of a typical cellphone. The cellphone may be operated in "airplane mode", and the app may enforce this as a restriction of use, in order to avoid potential interference between radio frequency emissions from the radio(s) within the phone and the PEMF. An exception may be the use of Bluetooth to communicate the signal to the device, though it is preferred to have no RF emissions from the phone during PEMF therapy. Because the PEMF is preferably generated based a square wave (a digital type signal), it may be possible to program a digital interface (e.g., USB) to generate the excitation signal for the device, rather than the audio output of the cellphone.

a downloadable smartphone app according to the present technology may be provided, having various interface screens. In the first screen, a splash screen may be provided. Typically, during PEMF therapy, it is desired to provide a relaxing environment, and the screens should be designed with muted colors, and avoidance of distractions. In the second screen, a set of different programs may be provided, which generate different output excitation signal patterns, such as "pain relief", "muscle tension", and "relaxation". The interface may also provide a user history option and a setup option. The "pain relief" screen is exemplary, and may include relevant user-identification information (name, birthdate, gender), body location to be treated, an intensity control slider, a PEMF therapy duration input, and a "start" screen button. This screen input may be used to represent a pre-treatment (subjective) evaluation of the patient condition.

During therapy, soothing patterns which optionally correspond to the treatment protocol may be shown on the screen, and may be animated accordingly.

A personalized user screen may show a summary of a treatment session, and provide a control button to stop the therapy. The app may also sense when the device is removed from the headphone jack, and preferably immediately cease generation of the excitation signal to avoid driving the internal phone speaker with the square wave pulses. The screen may provide an input for the patient to provide a post-treatment (subjective) evaluation, which can be used to track the therapy.

The app can also receive input from the user, post treatment, to provide subjective response factors. In some cases, objective data may be available. For example, where a vascular response to the therapy occurs, skin color, temperature, edema measurements, etc., may be acquired either automatically or manually, and input into the system. These inputs, wither on an individual basis or on a population basis, may be used to tailor the therapy for the individual, for example by changing pulse frequency and/or duty cycle, pulse amplitude, therapy duration, or various patterns of excitation pulses. In some cases, the therapy may be responsive to the environment, for example, ambient temperature or illumination, and the smartphone can detect these parameters.

It is believed that various forms of musical phrasing, in particular styles of classical music, are particularly appropriate for PEMF. Therefore, the excitation parameters may model classic works, such as patterns and amplitudes of excitation pulses, combinations of excitation parameters (similar to musical chords), etc. As discussed above, it is unclear that the peripheral tissues are capable of particularly responding to these signals, but rather that communications from the periphery to the central nervous system are involved.

What is claimed is:

1. A magnetic field therapy device, comprising:
   a conductive coil having an external diameter of between 2 mm and 20 mm and having between 5 and 200 turns;

a filter having at least one pole at about 3 kHz, configured to filter the oscillating electrical signal supplied to the conductive coil;

an input configured to:
receive an oscillating electrical signal having a frequency range comprising 0.1 Hz to 100 kHz, to supply a current to the conductive coil, and thereby generate an oscillating magnetic field surrounding the conductive coil; and a cover, surrounding the conductive coil, adapted separate the conductive coil from contact with an adjacent tissue substantially without disrupting a penetration of a magnetic field emitted from the conductive coil into the tissue, wherein under excitation by the oscillating electrical signal at a voltage of 1 V peak-to-peak at 100 Hz, a magnetic field of between 0.01 mTesla and 5 mTesla is obtained within the adjacent human or animal tissue at a depth of 1 cm from the cover.

2. The magnetic field therapy device according to claim 1, wherein the conductive coil has an inner diameter of between 5 mm and 10 mm.

3. The magnetic field therapy device according to claim 1, wherein the conductive coil has an outer diameter of less than or equal to 15 mm.

4. The magnetic field therapy device according to claim 1, wherein the presented impedance is at least 30 Ohms and less than 100 Ohms at 100 Hz.

5. The magnetic field therapy device according to claim 1, in combination with a signal generator configured to generate the oscillating electrical signal, having a frequency range comprising 50 Hz.

6. The magnetic field therapy device according to claim 1, wherein the cover comprises a spherical surface having a diameter of about 2 cm.

7. The magnetic field therapy device according to claim 1, wherein the input comprises at least one of an analog phono jack, a digital audio connector, and a radio frequency receiver, the magnetic field therapy device further comprising a self-contained battery power source to power the radio frequency receiver and the conductive coil.

8. The magnetic field therapy device according to claim 1, wherein the input is adapted to receive a signal from a smartphone.

9. The magnetic field therapy device according to claim 8, in combination with the smartphone, wherein the smartphone is configured to generate the oscillating electrical signal based on a downloadable app which executes under a smartphone operating system.

10. The magnetic field therapy device according to claim 9, wherein the smartphone is configured to execute the downloadable app in airplane mode, substantially without emission of radio frequency signals in excess of 25 MHz.

11. A magnetic field therapy method, comprising:
providing a conductive coil, an input configured to receive an oscillating electrical signal and to supply a current to the conductive coil, to thereby generate an oscillating magnetic field surrounding the conductive coil, and a cover, surrounding the conductive coil, adapted to contact human or animal skin and pass the oscillating magnetic field to the animal or human skin substantially without distortion or attenuation;
generating the oscillating electrical signal in a first state with a smartphone under control of a smartphone app; and
emitting the generated oscillating magnetic field surrounding the conductive coil into the human or animal skin adjacent to the cover, comprising a magnetic field oscillation frequency within a range of 0.1 Hz to 100 kHz, having a magnetic field strength of between 0.01 mTesla and 50 mTesla at a distance of 1 cm from the cover.

12. The method according to claim 11, further comprising:
receiving a user input to the smartphone; and
generating the oscillating electrical signal in a second state with the smartphone under control of the smartphone app, the second state comprising a different distribution of frequencies of the oscillating electrical signal than the first state.

13. The method according to claim 11, wherein the generated oscillating magnetic field surrounding the conductive coil is emitted, under excitation by the oscillating electrical signal at a voltage of 1 V peak-to-peak, the magnetic field strength of between 0.01 mTesla and 5 mTesla in a human or animal tissue under the human or animal skin contacting the cover at a depth of 1 cm, aligned with an axis of the conductive coil.

14. The method according to claim 11, further comprising filtering the oscillating electrical signal generated by the smartphone under control of the smartphone app with an electrical filter disposed within the cover.

15. The method according to claim 14, wherein the electrical filter comprises a circuit board having at least one resistor and at least one capacitor.

16. The method according to claim 11, further comprising generating, on a display of the smartphone, an indication of at least a direction in which the cover should be moved over the human or animal skin.

17. The method according to claim 11, wherein the oscillating electrical signal is a square wave signal.

18. A pulsed electromagnetic field therapy system, comprising:
a device comprising:
an interface configured to receive an oscillating electrical signal within a frequency range of 0.1 Hz to 100 kHz from a smartphone;
a coiled conductor, having between 5 turns and 200 turns, and an inner diameter of between about 4-15 mm;
a filter having a pole
a cover, having an outer surface configured for contact with human or animal skin, which does not substantially interfere with a magnetic field emitted by the coiled conductor; and
a circuit within the cover, configured to excite the coiled conductor with a current corresponding to the oscillating electrical signal, to generate a magnetic field of between about 10 µTesla and 5 mTesla at a distance of 1 cm from the cover at a position axially aligned with the coiled conductor; and
the smartphone having a smartphone operating system, configured present the oscillating electrical signal, under control of a downloadable app which executes under the smartphone operating system, in airplane mode, substantially without emission of radio frequency signals in excess of 25 MHz.

19. The pulsed electromagnetic field therapy system according to claim 18, wherein the device further comprises a filter having at least one pole at about 3 kHz, configured to filter the oscillating electrical signal supplied to the coiled conductor.

20. The pulsed electromagnetic field therapy system according to claim 18, wherein the cover comprises a spherical surface having a diameter of about 2 cm, and the interface comprises at least one of an analog phono jack and a digital audio connector.

\* \* \* \* \*